(12) United States Patent
Cho

(10) Patent No.: US 8,686,115 B2
(45) Date of Patent: Apr. 1, 2014

(54) COMPOSITIONS AND METHODS FOR QUANTITATIVELY MONITORING LIPIDS

(75) Inventor: Wonhwa Cho, Lisle, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 63 days.

(21) Appl. No.: 13/508,381

(22) PCT Filed: Nov. 5, 2010

(86) PCT No.: PCT/US2010/055606
§ 371 (c)(1),
(2), (4) Date: May 7, 2012

(87) PCT Pub. No.: WO2011/057063
PCT Pub. Date: May 12, 2011

(65) Prior Publication Data
US 2012/0225447 A1    Sep. 6, 2012

Related U.S. Application Data

(60) Provisional application No. 61/258,959, filed on Nov. 6, 2009.

(51) Int. Cl.
*C07K 1/00*    (2006.01)

(52) U.S. Cl.
USPC .......................................... 530/350; 530/402

(58) Field of Classification Search
None
See application file for complete search history.

(56) References Cited

PUBLICATIONS

Ory, J.J. and Banaszak L.J., Biophysical Journal, Aug. 1999, vol. 77, pp. 1107-1116.
Avdulov, A.N. et al., Journal of Neurochemistry, 1997, vol. 69, pp. 1746-1752.

*Primary Examiner* — Suzanne M Noakes
*Assistant Examiner* — Jae W Lee
(74) *Attorney, Agent, or Firm* — Polsinelli PC; Teddy C. Scott, Jr.; Ron Galant

(57) ABSTRACT

Provided herein are fluorescent lipid binding proteins (FLBPs). The FLBPs comprise a lipid binding domain linked to a fluorophore, whrereby the fluorophore's fluorescence emission undergoes a spectral change upon lipid binding. the fluorophore is selected from the group consisting of 2-dimethylamino-6-acyl-naphthalene (DAN) and RED fluorophore and the lipid binding protein is selected from the group consisting of ENTH domain of epsin 1, C2 domain of bovine lactadherin, C 1B domain of protein kinase C-gamma, C2 domain of cytosolic phospholipase A2-beta, and PH domain of Bruton's tyrosine kinase PH.

33 Claims, 13 Drawing Sheets

A: Lact-C2-W26C-DAN (PS specific)

B: Lact-C2-W26C/D80R/H83E/Q85K-DAN (PA-selective)

REK = Lact-C2-W26C/D80R/H83E/Q85K-DAN

SEQUENCE LISTING

```
<160> NUMBER OF SEQ ID NOS: 11

<210> SEQ ID NO 1
<211> LENGTH: 158
<212> TYPE: PRT
<213> ORGANISM: Artificial Sequence
<220> FEATURE:
<223> OTHER INFORMATION: ENTH domain of Epsin 1.

<400> SEQUENCE: 1

Met Ser Thr Ser Ser Leu Arg Arg Gln Met Lys Asn Ile Val His Asn
1               5                   10                  15

Tyr Ser Glu Ala Glu Ile Lys Val Arg Glu Ala Thr Ser Asn Asp Pro
            20                  25                  30

Trp Gly Pro Ser Ser Ser Leu Met Ser Glu Ile Ala Asp Leu Thr Tyr
        35                  40                  45

Asn Val Val Ala Phe Ser Glu Ile Met Ser Met Ile Trp Lys Arg Leu
    50                  55                  60

Asn Asp His Gly Lys Asn Trp Arg His Val Tyr Lys Ala Met Thr Leu
65                  70                  75                  80

Met Glu Tyr Leu Ile Lys Thr Gly Ser Glu Arg Val Ser Gln Gln Cys
                85                  90                  95

Lys Glu Asn Met Tyr Ala Val Gln Thr Leu Lys Asp Phe Gln Tyr Val
            100                 105                 110

Asp Arg Asp Gly Lys Asp Gln Gly Val Asn Val Arg Glu Lys Ala Lys
        115                 120                 125

Gln Leu Val Ala Leu Leu Arg Asp Glu Asp Arg Leu Arg Glu Glu Arg
    130                 135                 140

Ala His Ala Leu Lys Thr Lys Glu Lys Leu Ala Gln Thr Ala
145                 150                 155

<210> SEQ ID NO 2
<211> LENGTH: 158
<212> TYPE: PRT
<213> ORGANISM: Artificial Sequence
<220> FEATURE:
<223> OTHER INFORMATION: Modified ENTH domain of Epsin 1.

<400> SEQUENCE: 2

Met Ser Thr Trp Ser Leu Arg Arg Gln Cys Lys Asn Ile Val His Asn
1               5                   10                  15

Tyr Ser Glu Ala Glu Ile Lys Val Arg Glu Ala Thr Ser Asn Asp Pro
            20                  25                  30

Trp Gly Pro Ser Ser Ser Leu Met Ser Glu Ile Ala Asp Leu Thr Tyr
        35                  40                  45

Asn Val Val Ala Phe Ser Glu Ile Met Ser Met Ile Trp Lys Arg Leu
```

```
                50             55              60
Asn Asp His Gly Lys Asn Trp Arg His Val Tyr Lys Ala Met Thr Leu
65                  70                  75                  80

Met Glu Tyr Leu Ile Lys Thr Gly Ser Glu Arg Val Ser Gln Gln Ala
                85                  90                  95

Lys Glu Asn Met Tyr Ala Val Gln Thr Leu Lys Asp Phe Gln Tyr Val
                100                 105                 110

Asp Arg Asp Gly Lys Asp Gln Gly Val Asn Val Arg Glu Lys Ala Lys
                115                 120                 125

Gln Leu Val Ala Leu Arg Asp Glu Asp Arg Leu Arg Glu Glu Arg
                130                 135                 140

Ala His Ala Leu Lys Thr Lys Glu Lys Leu Ala Gln Thr Ala
145                 150                 155

<210> SEQ ID NO 3
<211> LENGTH: 158
<212> TYPE: PRT
<213> ORGANISM: Artificial Sequence
<220> FEATURE:
<223> OTHER INFORMATION: C2 domain of bovine lactadherin.

<400> SEQUENCE: 3

Cys Thr Glu Pro Leu Gly Leu Lys Asp Asn Thr Ile Pro Asn Lys Gln
1               5                   10                  15

Ile Thr Ala Ser Ser Tyr Tyr Lys Thr Trp Gly Leu Ser Ala Phe Ser
                20                  25                  30

Trp Phe Pro Tyr Tyr Ala Arg Leu Asp Asn Gln Gly Lys Phe Asn Ala
                35                  40                  45

Trp Thr Ala Gln Thr Asn Ser Ala Ser Glu Trp Leu Gln Ile Asp Leu
                50                  55                  60

Gly Ser Gln Lys Arg Val Thr Gly Ile Ile Thr Gln Gly Ala Arg Asp
65                  70                  75                  80

Phe Gly His Ile Gln Tyr Val Ala Ala Tyr Arg Val Ala Tyr Gly Asp
                85                  90                  95

Asp Gly Val Thr Trp Thr Glu Tyr Lys Asp Pro Gly Ala Ser Glu Ser
                100                 105                 110

Lys Ile Phe Pro Gly Asn Met Asp Asn Asn Ser His Lys Lys Asn Ile
                115                 120                 125

Phe Glu Thr Pro Phe Gln Ala Arg Phe Val Arg Ile Gln Pro Val Ala
                130                 135                 140

Trp His Asn Arg Ile Thr Leu Arg Val Glu Leu Leu Gly Cys
145                 150                 155

<210> SEQ ID NO 4
<211> LENGTH: 158
<212> TYPE: PRT
<213> ORGANISM: Artificial Sequence
<220> FEATURE:
<223> OTHER INFORMATION: Modified C2 domain of bovine lactadherin.

<400> SEQUENCE: 4

Cys Thr Glu Pro Leu Gly Leu Lys Asp Asn Thr Ile Pro Asn Lys Gln
1               5                   10                  15

Ile Thr Ala Ser Ser Tyr Tyr Lys Thr Cys Gly Leu Ser Ala Phe Ser
                20                  25                  30

Trp Phe Pro Tyr Tyr Ala Arg Leu Asp Asn Gln Gly Lys Phe Asn Ala
                35                  40                  45

Trp Thr Ala Gln Thr Asn Ser Ala Ser Glu Trp Leu Gln Ile Asp Leu
```

```
                  50                  55                  60
Gly Ser Gln Lys Arg Val Thr Gly Ile Ile Thr Gln Gly Ala Arg Asp
 65                  70                  75                  80

Phe Gly His Ile Gln Tyr Val Ala Ala Tyr Arg Val Ala Tyr Gly Asp
                 85                  90                  95

Asp Gly Val Thr Trp Thr Glu Tyr Lys Asp Pro Gly Ala Ser Glu Ser
                100                 105                 110

Lys Ile Phe Pro Gly Asn Met Asp Asn Asn Ser His Lys Lys Asn Ile
                115                 120                 125

Phe Glu Thr Pro Phe Gln Ala Arg Phe Val Arg Ile Gln Pro Val Ala
                130                 135                 140

Trp His Asn Arg Ile Thr Leu Arg Val Glu Leu Leu Gly Cys
145                 150                 155

<210> SEQ ID NO 5
<211> LENGTH: 158
<212> TYPE: PRT
<213> ORGANISM: Artificial Sequence
<220> FEATURE:
<223> OTHER INFORMATION: Modified C2 domain of bovine lactadherin.

<400> SEQUENCE: 5

Cys Thr Glu Pro Leu Gly Leu Lys Asp Asn Thr Ile Pro Asn Lys Gln
  1               5                  10                  15

Ile Thr Ala Ser Ser Tyr Tyr Lys Thr Cys Gly Leu Ser Ala Phe Ser
                 20                  25                  30

Trp Phe Pro Tyr Tyr Ala Arg Leu Asp Asn Gln Gly Lys Phe Asn Ala
                 35                  40                  45

Trp Thr Ala Gln Thr Asn Ser Ala Ser Glu Trp Leu Gln Ile Asp Leu
 50                  55                  60

Gly Ser Gln Lys Arg Val Thr Gly Ile Ile Thr Gln Gly Ala Arg Arg
 65                  70                  75                  80

Phe Gly Glu Ile Lys Tyr Val Ala Ala Tyr Arg Val Ala Tyr Gly Asp
                 85                  90                  95

Asp Gly Val Thr Trp Thr Glu Tyr Lys Asp Pro Gly Ala Ser Glu Ser
                100                 105                 110

Lys Ile Phe Pro Gly Asn Met Asp Asn Asn Ser His Lys Lys Asn Ile
                115                 120                 125

Phe Glu Thr Pro Phe Gln Ala Arg Phe Val Arg Ile Gln Pro Val Ala
                130                 135                 140

Trp His Asn Arg Ile Thr Leu Arg Val Glu Leu Leu Gly Cys
145                 150                 155

<210> SEQ ID NO 6
<211> LENGTH: 50
<212> TYPE: PRT
<213> ORGANISM: Artificial Sequence
<220> FEATURE:
<223> OTHER INFORMATION: C1B domain of protein kinase C gamma.

<400> SEQUENCE: 6

His Lys Phe Arg Leu His Ser Tyr Ser Ser Pro Thr Phe Cys Asp His
  1               5                  10                  15

Cys Gly Ser Leu Leu Tyr Gly Leu Val His Gln Gly Met Lys Cys Ser
                 20                  25                  30

Cys Cys Glu Met Asn Val His Arg Arg Cys Val Arg Ser Val Pro Ser
                 35                  40                  45

Leu Cys
```

```
<210> SEQ ID NO 7
<211> LENGTH: 50
<212> TYPE: PRT
<213> ORGANISM: Artificial Sequence
<220> FEATURE:
<223> OTHER INFORMATION: Modified C1B domain of protein kinase C gamma.

<400> SEQUENCE: 7

His Lys Phe Arg Leu His Ser Tyr Ser Ser Pro Thr Phe Cys Asp His
1               5                   10                  15

Cys Gly Ser Leu Leu Tyr Gly Cys Val His Gln Gly Met Lys Cys Ser
            20                  25                  30

Ser Cys Glu Met Asn Val His Arg Arg Cys Val Arg Ser Val Pro Ser
        35                  40                  45

Leu Cys
    50

<210> SEQ ID NO 8
<211> LENGTH: 120
<212> TYPE: PRT
<213> ORGANISM: Artificial Sequence
<220> FEATURE:
<223> OTHER INFORMATION: C2 domain of cytosolic phospholipase A2beta.

<400> SEQUENCE: 8

Thr Cys Leu Leu Thr Val Arg Val Leu Gln Ala His Arg Leu Pro Ser
1               5                   10                  15

Lys Asp Leu Val Thr Pro Ser Asp Cys Tyr Val Thr Leu Trp Leu Pro
            20                  25                  30

Thr Ala Cys Ser His Arg Leu Gln Thr Arg Thr Val Lys Asn Ser Ser
        35                  40                  45

Ser Pro Val Trp Asn Gln Ser Phe His Phe Arg Ile His Arg Gln Leu
    50                  55                  60

Lys Asn Val Met Glu Leu Lys Val Phe Asp Gln Asp Leu Val Thr Gly
65                  70                  75                  80

Asp Asp Pro Val Leu Ser Val Leu Phe Asp Ala Gly Thr Leu Arg Ala
                85                  90                  95

Gly Glu Phe Arg Arg Glu Ser Phe Ser Leu Ser Pro Gln Gly Glu Gly
            100                 105                 110

Arg Leu Glu Val Glu Phe Arg Leu
        115                 120

<210> SEQ ID NO 9
<211> LENGTH: 120
<212> TYPE: PRT
<213> ORGANISM: Artificial Sequence
<220> FEATURE:
<223> OTHER INFORMATION: Modified C2 domain of cytosolic phospholipase
      A2beta.

<400> SEQUENCE: 9

Thr Cys Leu Leu Thr Val Arg Val Leu Gln Ala His Arg Leu Pro Ser
1               5                   10                  15

Lys Asp Leu Val Thr Pro Ser Asp Cys Tyr Val Thr Leu Trp Leu Pro
            20                  25                  30

Thr Ala Cys Ser His Arg Leu Gln Thr Arg Thr Val Lys Asn Ser Ser
        35                  40                  45

Ser Pro Val Trp Asn Gln Ser Phe His Phe Arg Ile His Arg Gln Leu
    50                  55                  60
```

```
Lys Asn Val Met Glu Leu Lys Val Phe Asp Gln Asp Cys Lys Thr Gly
 65                  70                  75                  80

Asp Asp Pro Val Cys Ser Lys Leu Phe Asp Ala Gly Thr Leu Arg Ala
                 85                  90                  95

Gly Glu Phe Arg Arg Glu Ser Phe Ser Leu Ser Pro Gln Gly Glu Gly
                100                 105                 110

Arg Leu Glu Val Glu Phe Arg Leu
        115                 120

<210> SEQ ID NO 10
<211> LENGTH: 169
<212> TYPE: PRT
<213> ORGANISM: Artificial Sequence
<220> FEATURE:
<223> OTHER INFORMATION: PH domain of Bruton's tyrosine kinase.

<400> SEQUENCE: 10

Ala Ala Val Ile Leu Glu Ser Ile Phe Leu Lys Arg Ser Gln Gln Lys
 1               5                  10                  15

Lys Lys Thr Ser Pro Leu Asn Phe Lys Lys Arg Leu Phe Leu Leu Thr
                20                  25                  30

Val His Lys Leu Ser Tyr Tyr Glu Tyr Asp Phe Glu Arg Gly Arg Arg
             35                  40                  45

Gly Ser Lys Lys Gly Ser Ile Asp Val Glu Lys Ile Thr Cys Val Glu
 50                  55                  60

Thr Val Val Pro Glu Lys Asn Pro Pro Glu Arg Gln Ile Pro Arg Arg
 65                  70                  75                  80

Arg Gly Glu Glu Ser Ser Glu Met Glu Gln Ile Ser Ile Ile Glu Arg
                 85                  90                  95

Phe Pro Tyr Pro Phe Gln Val Val Tyr Asp Glu Gly Pro Leu Tyr Val
                100                 105                 110

Phe Ser Pro Thr Glu Glu Leu Arg Lys Arg Trp Ile His Gln Leu Lys
            115                 120                 125

Asn Val Ile Arg Tyr Asn Ser Asp Leu Val Gln Lys Tyr His Pro Cys
130                 135                 140

Phe Trp Ile Asp Gly Gln Tyr Leu Cys Cys Ser Gln Thr Ala Lys Asn
145                 150                 155                 160

Ala Met Gly Cys Gln Ile Leu Glu Asn
                165

<210> SEQ ID NO 11
<211> LENGTH: 169
<212> TYPE: PRT
<213> ORGANISM: Artificial Sequence
<220> FEATURE:
<223> OTHER INFORMATION: Modified PH domain of Bruton's tyrosine kinase.

<400> SEQUENCE: 11

Ala Ala Val Ile Leu Glu Ser Ile Phe Leu Lys Arg Ser Gln Gln Lys
 1               5                  10                  15

Lys Lys Thr Ser Pro Leu Asn Phe Lys Lys Arg Leu Phe Leu Leu Thr
                20                  25                  30

Val His Lys Leu Ser Tyr Tyr Glu Tyr Asp Phe Cys Arg Gly Arg Arg
             35                  40                  45

Gly Ser Lys Lys Gly Ser Ile Asp Val Glu Lys Ile Thr Cys Val Glu
 50                  55                  60

Thr Val Val Pro Glu Lys Asn Pro Pro Glu Arg Gln Ile Pro Arg Arg
 65                  70                  75                  80
```

-continued

```
Arg Gly Glu Glu Ser Ser Glu Met Glu Gln Ile Ser Ile Ile Glu Arg
                 85              90              95
Phe Pro Tyr Pro Phe Gln Val Val Tyr Asp Glu Gly Pro Leu Tyr Val
            100             105             110
Phe Ser Pro Thr Glu Glu Leu Arg Lys Arg Trp Ile His Gln Leu Lys
        115             120             125
Asn Val Ile Arg Tyr Asn Ser Asp Leu Val Gln Lys Tyr His Pro Cys
        130             135             140
Phe Trp Ile Asp Gly Gln Tyr Leu Cys Cys Ser Gln Thr Ala Lys Asn
145             150             155             160
Ala Met Gly Cys Gln Ile Leu Glu Asn
                165
```

COMPOSITIONS AND METHODS FOR QUANTITATIVELY MONITORING LIPIDS

CROSS REFERENCE TO RELATED APPLICATIONS

This is the national stage of International Application No. PCT/US2010/055606, filed on Nov. 5, 2010, which claims to the benefit of U.S. Provisional Application No. 61/258,959, filed on Nov. 6, 2009, the contents of which are incorporated herein by reference.

FEDERALLY SPONSORED RESEARCH

This invention was made with government support under grant numbers GM76581 and GM68849 awarded by the National Institutes of Health. The government has certain rights in the invention.

FIELD OF THE INVENTION

The present invention relates to the development and use of lipid sensing agents to quantitatively track lipids in cells.

BACKGROUND

Many lipids control diverse cellular processes related to cell proliferation, apoptosis, metabolism and migration. Lipids, such as phosphoinositides, sphingolipids, and fatty acids, their binding partners, and/or their downstream targets may constitute complex signaling networks that control these processes, whereby imbalances in these networks may contribute to the pathogenesis of human diseases, such as inflammation, cancer, diabetes, and metabolic diseases.

Since lipids are continuously produced, degraded, and transported in a tightly controlled manner, determining their spatio-temporal fluctuation is necessary to understand lipid-mediated processes and for the development of new strategies to diagnose, treat, and prevent human diseases caused by lipid-related processes. Genetically incorporated fluorescence protein-tagged lipid binding domains have been widely used as a probe or sensor for visualizing the spatiotemporal dynamics of various cellular lipids. Despite its experimental convenience and popularity, these methods do not provide quantitative information because fluorescence proteins do not undergo a spectral change upon lipid binding. To overcome this limitation, fluorescence resonance energy transfer (FRET)-based methods using a pair of fluorescence proteins, such as cyan and yellow proteins, have been devised. However, these methods generally suffer from low sensitivity and robustness in in situ lipid quantification. Furthermore, lipid sensors made of naturally occurring lipid binding domains may not be able to compete with those endogenous cellular proteins with higher affinity for and/or easier access to particular lipids. Although mass spectrometry-based lipid analysis offers higher sensitivity and provides the detailed structural information about lipids, including acyl chain compositions, the current method requires physical separation of lipids from cells and thus can provide neither spatial nor real-time temporal information.

Accordingly, lipid binding proteins that have a higher lipid selectivity and membrane affinity than wild-type lipid binding domains, minimal affinity for cellular proteins, and which can be easily tracked in a cell or vesicle are desired. More specifically, fluorescent lipid binding proteins (FLBPs) that are amenable to delivery into mammalian cells and subsequent imaging and quantitative studies are desired. Such compositions will allow for a better understanding of the molecular mechanisms underlying lipid turnover and lipid-related diseases.

SUMMARY OF THE INVENTION

Provided herein is a fluorescent lipid-binding protein (FLBP). The FLBP may comprise a fluorophore linked to a lipid binding domain or protein. The FLBP may comprise 2-dimethylamino-6-acyl-naphthalene (DAN) and the ENTH domain of epsin 1 or a fragment thereof. See SEQ ID NO:1. The amino acid sequence of the ENTH domain or fragment thereof may comprise one or more of the following substitutions: M10C, C96A, and S4W (engineered ENTH or eENTH). The ENTH domain may comprise all three substitutions. See SEQ ID NO:2. DAN may be linked to the eENTH domain via amino acid C10.

The FLBP may comprise a DAN labeled C2 domain of bovine lactadherin (DAN-Lact-C2). The C2 domain may comprise SEQ ID NO:3, or a fragment thereof. The SEQ ID NO:3, or a fragment thereof, may comprise one or more of the following substitutions: W26C, D80R, H83E, and/or Q85K. The Lact-C2 may comprise all four substitutions.

The FLBP may comprise a DAN labeled C1B domain of protein kinase Cγ. The C1B domain may comprise SEQ ID NO:6, or a fragment thereof. The SEQ ID NO:6, or a fragment thereof, may comprise one or both of the following mutations: L24C and/or C33S.

The FLBP may comprise a DAN labeled C2 domain of cytosolic phospholipase A2β. The C2 domain of cytosolic phospholipase may comprise SEQ ID NO:8, or a fragment thereof. The SEQ ID NO:8, or a fragment thereof, may comprise one or both of the following mutations: L85C and/or V87K.

The FLBP may comprise a DAN labeled PH domain of Bruton's tyrosine kinase. The PH domain may comprise SEQ ID NO:10, or a fragment thereof. The SEQ ID NO:10, or a fragment thereof, may comprise the following mutation: E45C.

Also provided herein is a method for quantifying a target lipid in a cell or lipid vesicle. The target lipid may be phosphatidylinositol-4,5-bisphosphate (PtdIns(4,5)P$_2$), phosphatidylserine, phosphatidic acid, diacylglycerol, cardiolipin, and/or phosphatidylinositol-3,4,5-triphosphate in a cell membrane or lipid vesicle. The method may comprise administering the FLBP to a cell or vesicle, imaging the cell or vesicle, and then quantifying PtdIns(4,5)P$_2$, phosphatidylserine, phosphatidic acid, diacylglycerol, cardiolipin, and/or phosphatidylinositol-3,4,5-triphosphate in the cell membrane or vesicle. The FLBP may be introduced to the cell via microinjection or transfection with a lipid formulation. The lipid formulation may be a BIOPORTER® formulation. The cell or vesicle may be imaged by an imaging system such as fluorescence microscopy, confocal microscopy and/or two-photon microscopy. Based on the cell or vesicle image, ratiometric analyses may be performed to quantify the PtdIns(4,5)P$_2$, phosphatidylserine, phosphatidic acid, diacylglycerol, cardiolipin, and/or phosphatidylinositol-3,4,5-triphosphate in the cell membrane or vesicle. Scanning fluorescence correlation spectroscopy (sFCS) may be used for quantifying lipids.

Also provided herein is a method of diagnosing a lipid metabolizing enzyme disorder, such as a PI-3 kinase-related disorder. The method may comprise introducing the FLBP to a sample derived from a subject; imaging cells in the sample; quantifying the target lipid in the cells; and then comparing the quantity identified in the imaged cells with a reference standard. The quantity of target lipid present in the reference standard may be the quantity present in a comparable sample from an individual with or without the disorder. The disorder may be a cancer or a lipid metabolism disorder.

BRIEF DESCRIPTION OF THE DRAWINGS

FIG. 7a shows angular profiles of [PtdIns(4,5)P2]s in the plasma membrane of NIH 3T3 cells at different times.

FIG. 7b shows a time averaging (for 20 minutes) of the angular profiles shown in FIG. 7a.

FIG. 8c shows the angular profile representation of the local [PtdIns(4,5)P2]s before (orange) and 2 minutes after (cyan) insulin stimulation.

FIG. 8d shows the time courses of spatially averaged [PtdIns(4,5)P2]s in the PM upon 1 μM insulin treatment.

DETAILED DESCRIPTION

Figure 1:
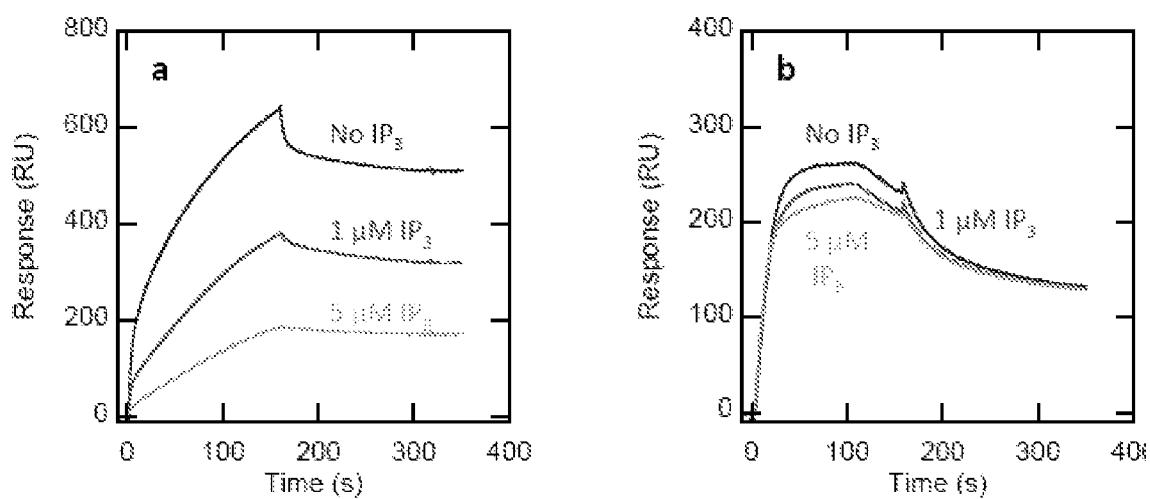
FIG. 1(a) shows an SPR sensorgram of the PLCδ PH domain (250 nM) in the presence of 0, 1 and 5 μM of inositol-(1,4,5)-triphosphate ($IP_3$).
FIG. 1(b) shows an SPR sensorgram of DAN-eENTH (50 nM) in the presence of 0, 1 and 5 μM of $IP_3$.

The inventors have discovered that certain lipid binding domains or proteins may be fluorescently labeled with one or more fluorophores and subsequently used to quantify specific target lipids. More specifically, these FLBPs may be administered to a cell, whereby the cell is imaged and the target lipid is quantified. Accordingly, the general structure of a FLBP-bound target lipid complex is as follows:

Fluorophore—Lipid Binding Domain or Protein—Target Lipid.

The fluorophore of the FLBP may be any fluorophore, such as 2-dimethylamino-6-acyl-naphthalene (DAN) or red fluorophore (RED). The fluorophore is linked to a lipid binding protein, which may be a lipid binding fragment of any protein. The modular nature of the FLBP may allow for different fluorophores to be linked to different lipid binding domains or proteins.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Fragment

"Fragment" as used herein may mean a portion of a reference peptide or polypeptide or nucleic acid sequence.

2. Fluorophore—Lipid Binding Domain or Protein—Target Lipid a. Fluorophore

The fluorophore of the FLBP may be any fluorophore. The fluorophore may be a molecule which will absorb energy of a specific wavelength and re-emit energy at a different wavelength. The amount and wavelength of the emitted energy may depend on both the fluorophore and the chemical environment of the fluorophore. Examples of such fluorophores are DAN and RED.

(1) DAN

DAN may be an environmentally sensitive fluorophore. DAN may exhibit a difference in fluorescence emission when transferred from an aqueous environment to a non-polar environment. DAN may exhibit an increase in fluorescence emission when transferred from an aqueous environment to a non-polar environment. When linked to a lipid binding domain or protein, such as eENTH, DAN may increase the affinity of the lipid binding domain or protein for cell membrane and/or the target lipid. In addition, DAN-Lipid binding domain or protein may not deform the membrane and/or the target lipid to which it binds.

(2) Red Fluorophore

The fluorophore may be a red fluorophore ("RED") having the following structure:

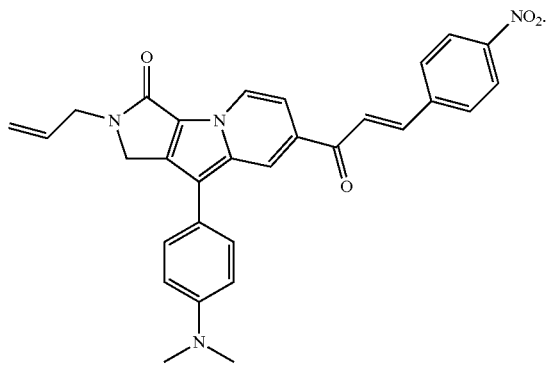 [SMILES: C=CCN1Cc2c(-c3ccc(N(C)C)cc3)c3cc(C(=O)/C=C/c4ccc([N+](=O)[O-])cc4)ccn3c2C1=O]

RED may be an environmentally sensitive fluorophore. RED may exhibit a difference in fluorescence emission when transferred from an aqueous environment to a non-polar environment. RED may exhibit an increase in fluorescence emission when transferred from an aqueous environment to a non-polar environment. When linked to a lipid binding domain or protein (RED-LBD), RED may increase the affinity of the LBD for cell membrane and/or the target lipid. In addition, RED-LBD may not deform the membrane and/or the target lipid to which it binds.

b. Lipid Binding Domain or Protein

The lipid binding domain or protein may be any protein or fragment thereof that binds to a lipid. Examples include the following.

(1) ENTH Domain of Epsin 1

The ENTH domain of Epsin 1 may comprise the amino acid sequence shown in SEQ ID NO:1. This sequence may be modified (eENTH). eENTH may be derived from SEQ ID NO:1. eENTH may comprise SEQ ID NO:1 having one or more amino acid substitutions. The one or more amino acid substitutions may, singly or in combination, suppress any affinity that wild-type ENTH or eENTH may have for another lipid. The one or more amino acid substitutions may, singly or in combination, direct where DAN is linked to ENTH. The one or more amino acid substitutions may be selected from the group consisting of M10C, C96A, and/or S4W. eENTH may comprise amino acids 1-158 of SEQ ID NO:2, or a fragment thereof.

(2) C2 Domain of Lactadherin (Lact-C2)

The Lact-C2 domain may comprise the amino acid sequence shown in SEQ ID NO:3. Lact-C2 may be modified (eLact-C2). eLact-C2 may be derived from SEQ ID NO:3. eLact-C2 may comprise SEQ ID NO:3 having one or more amino acid substitutions. The one or more amino acid substitutions may, singly or in combination, suppress any affinity that wild-type Lact-C2 or eLact-C2 may have for a lipid other than phosphatidylserine or phosphatidic acid. The one or more amino acid substitutions may, singly or in combination, direct where a fluorophore is linked to Lact-C2. The one or more amino acid substitutions may be selected from the group consisting of W26C, D80R, H83E and/or Q85K. eLact-C2 may comprise amino acids 1-158 of SEQ ID NO:4, or a fragment thereof. eLact-C2 may comprise amino acids 1-158 of SEQ ID NO:5, or a fragment thereof.

(3) C1B Domain of Protein Kinase Cγ (PKCγ-C1B)

The C1B domain of PKCγ may comprise the amino acid sequence shown in SEQ ID NO:6. This sequence may be modified (ePKCγ-C1B). ePKCγ-C1B may be derived from SEQ ID NO:6. ePKCγ-C1B may comprise SEQ ID NO:6 having one or more amino acid substitutions. The one or more amino acid substitutions may, singly or in combination, suppress any affinity that the wild typeCiB domain of PKCγ or ePKCγ-C1B may have for another lipid. The one or more amino acid substitutions may, singly or in combination, remove a free cystein. The one or more amino acid substitutions may, singly or in combination, direct where a fluorophore is linked to PKCγ-C1B. The one or more amino acid substitutions may be selected from the group consisting of L24C and/or C33S. ePKCγ-C1B may comprise amino acids 1-50 of SEQ ID NO:7, or a fragment thereof.

(4) C2 Domain of Cytosolic Phospholipase A₂β (cPLA₂β-C2)

The C2 domain of cPLA₂β may comprise the amino acid sequence shown in SEQ ID NO:8. This sequence may be modified (ecPLA₂β-C2). ecPLA₂β-C2 may be derived from SEQ ID NO:8. ecPLA₂β-C2 may comprise SEQ ID NO:8 having one or more amino acid substitutions. The one or more amino acid substitutions may, singly or in combination, suppress any affinity that wild-type cPLA₂β-C2 or ecPLA₂β-C2 may have for another lipid. The one or more amino acid substitutions may, singly or in combination, direct where a fluorophore is linked to ecPLA₂β-C2. The one or more amino acid substitutions may be selected from the group consisting of L85C and/or V86K. ecPLA₂β-C2 may comprise amino acids 1-120 of SEQ ID NO:9, or a fragment thereof.

(5) PH Domain of Bruton's Tyrosine Kinase PH (Btk-PH)

The PH domain of Btk may comprise the amino acid sequence shown in SEQ ID NO:10. This sequence may be modified (eBTK-PH). eBTK-PH may be derived from SEQ ID NO:10. eBTK-PH may comprise SEQ ID NO:10 having one or more amino acid substitutions. The one or more amino acid substitutions may, singly or in combination, suppress any affinity that the wild type PH domain of Btk or eBTK-PH may have for another lipid. The one or more amino acid substitutions may, singly or in combination, direct where a fluorophore is linked to eStk-PH. The one or more amino acid substitutions may be selected from the group consisting of E45C. eStk-PH may comprise amino acids 1-165 of SEQ ID NO:11, or a fragment thereof.

c. Target Lipid

The target lipid may be any lipid that is desired to be indentified and/or quantified. For example, the target lipid may be a phospholipid that is composed of a polar head and one or more non-polar tails. The phospholipid may be amphipathic and contain a hydrophilic head and one or more hydrophobic tails.

The target lipid for fluorophore-eENTH may be phosphatidylinositol 4,5-bisphosphate ("PtdIns(4,5)$P_2$") The target lipid for fluorophore-eLact-C2 may be phosphatidylserine (PS) or phosphatidic acid (PA). The target lipid for fluorophore-ePKCγ-C1B may be diacylglycerol (DAG). The target lipid for fluorophore-ecPLA2γ-C2 may be cardiolipin (CL). The target lipid for fluorophore-eStk-PH may be phosphatidylinositol 3,4,5-trisphosphate (PtdIns(3,4,5)$P_3$). PtdIns(4,5)$P_2$, PS, PA, DAG, CL, and/or PtdIns(3,4,5)$P_3$ may be cytosolic or in a membrane. The membrane may be a cellular membrane or in the form of a lipid vesicle. The lipid vesicle may be a large unilamellar vesicle (LUV), whereby the diameter of the vesicle is between about 60 nm and 800 nm, 70 nm and 800, 80 nm and 800 nm, 90 nm and 800 nm, 100 nm and 700 nm, 200 nm and 600 nm, 300 nm and 500 nm, 400 nm and 800 nm, 500 nm and 800 nm, 600 nm and 800 nm, or 700 nm and 800 nm. The lipid vesicle may be a giant unilamellar vesicle (GUV), whereby the diameter of the vesicle is between about 1 μm and 50 μm, 5 μm and 50 μm, 10 μm and 50 μm, 15 μm and 50 μm, 20 μm and 50 μm, 25 μm and 50 μm, 30 μm and 50 μm, or 40 μm and 50 μm.

The cellular membrane may be a eukaryote cell membrane. The eukaryote cell membrane may be mammalian. The mammalian cell membrane may be a structural component of a fibroblast, a keratinocyte, a monocyte, a macrophage, an epithelial cell, a muscle cell, or a nerve cell. The fibroblast may be a NIH-3T3 cell.

The FLBP may be administered to a sample, cell, or vesicle, whereby the cell is imaged and target PS, PtdIns(4,5)$P_2$, DAG, CL, and/or PtdIns(3,4,5)$P_3$ is quantified.

3. Exemplified FLBPs and Target Lipids a. DAN-eENTH—PtdIns(4,5)$P_2$

Provided herein is an ENTH domain of epsin1, which is linked to 2-dimethylamino-6-acyl-naphthalene (DAN). The ENTH domain contains 3 mutations, which are substitutions: M10C, C96A, and S4W. See SEQ ID NO:2. This DAN-eENTH (M10C, C96A, S4W) is an exceptional, high-affinity phosphatidylinositol-4,5-bisphosphate (PtdIns(4,5)$P_2$)-binding protein.

b. DAN-eLact-C2(W26C)—Phosphatidic Acid

Provided herein is a C2 domain of bovine lactadherin, which is linked to 2-dimethylamino-6-acyl-naphthalene (DAN). The C2 domain contains a single mutation, which is a subsitution: W26C. See SEQ ID NO: 4. This DAN-eLACT-C2 (W26C) reagent is an exceptional, high-affinity phosphatidic acid-binding protein.

c. DAN-eLact-C2(W26C, D80R, H83E, Q85K)—Phosphatidylserine

Provided herein is another C2 domain of bovive lactadherin, which is linked to 2-dimethylamino-6-acyl-naphthalene (DAN). The C2 domain contains 4 mutations, which are substitutions: W26C, D80R, H83E, and Q85K. See SEQ ID NO:5. This DAN-eLACT-C2 (W26C, D80R, H83E, Q85K) is an exceptional, high-affinity phosphatidylserine-binding protein.

d. DAN-ePKCγ-C1B-Diacylglycerol

Provided herein is a C1B domain of PKCγ-C1B, which is linked to 2-dimethylamino-6-acyl-naphthalene (DAN). The C1B domain contains 2 mutations, which are substitutions: L24C and C33S. See SEQ ID NO:7. This DAN-ePKC2γ-C1B (L24C, C33S) is an exceptional, high-affinity diacylglycerol (DAG)-binding protein.

e. DAN-ecPLA2β-C2-Cardiolipin

Provided herein is a C2 domain of cPLA$_2$β, which is linked to 2-dimethylamino-6-acyl-naphthalene (DAN). The C2 domain contains 2 mutations, which are substitutions: L85C and V86K. See SEQ ID NO:9. This DAN-ecPLA2β-C2 (L85C, V86K) is an exceptional, high-specificity cardiolipin (CL)-binding protein.

f. DAN-eStk-PH-PtdIns(3,4,5)$P_3$

Provided herein is a PH domain of Btk, which is linked to 2-dimethylamino-6-acyl-naphthalene (DAN). The PH domain contains 1 mutation, which is a substitution: E45C. See SEQ ID NO:11. This DAN-eStk-PH (E45C) is an exceptional, high-affinity phosphatidylinositol-3,4,5-triphosphate (PtdIns(3,4,5)$P_3$)-binding protein.

4. Method of Quantifying Target Lipid

Provided herein is a method of quantifying a target lipid. The FLBP may be administered or introduced to a biological sample, a cell or lipid vesicle, wherein the FLBP binds to a target lipid. The FLBP-bound target lipid complex may then be quantified based upon image analysis of the cell or lipid vesicle.

a. Administration

The FLBP may be administered or introduced to a biological sample, cell or lipid vesicle. The FLBP may be injected into the sample, cell or vesicle, or transfected into the sample, cell or vesicle via a protein transfection agent. The transfection agent may be an Influx® pinocytic cell-loading agent. The transfection agent may be a lipid formulation. The lipid formulation may be a BIOPORTER® transfection agent.

(1) Sample, Cell, or Vesicle

The sample comprise one or more cells and/or one or more lipid vesicles. The cell or lipid vesicle may be derived from any cell type, tissue, or bodily fluid from a subject. Such cell types, tissues, and fluid may include sections of tissues such as biopsy and autopsy samples, frozen sections taken for histologic purposes, blood, plasma, serum, sputum, stool, tears, mucus, saliva, hair, and skin. Cell types and tissues may also include lung tissue or cells, lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from a subject, but can also be accomplished by using previously isolated cells (e.g., isolated by another person, at another time, and/or for another purpose). Archival tissues, such as those having treatment or outcome history, may also be used.

b. Imaging

The FLBP-containing cell or lipid vesicle may be subjected to image analysis. Image analysis may involve the use of an imaging microscopy system. The imaging microscopy system may be fluorescence microscopy, confocal microscopy, and/or two-photon microscopy.

c. Quantification

The target lipid in a cell or lipid vesicle may be quantified via ratiometric analysis or calculation based on sFCS. With respect to ratiometric analysis, a calibration curve may be provided. The curve may be based on $F_B/F_G$ versus the target lipid, such as [PtdIns(4,5)$P_2$], wherein the F values are determined by photon counting, in corresponding different band pass filter channels, of imaged lipid vesicles or cells containing FLBP and having a known concentration of the target lipid and, optionally, one or more other lipids. The calibration curve may then be used to determine the concentration of the target lipid.

For cell/cell membrane measurements, minimum $F_B$ values may be taken from the cytosol and maximum $F_B$ values assessed after an excess amount of the target lipid is administered to the cell. Cellular [target lipid] may then be determined from the observed ($F_B/F_G$) values using the calibration curve described above.

d. Lipid Disorders and Cancer

The method of quantifying a target lipid may be used to diagnose a lipid metabolism disorder and/or a cancer. The disorder may be one that is associated with a lipid metabolizing enzyme, such as phosphoinositide 3 kinase (PI3K). The FLBP may be used to quantify a target lipid that is either metabolized by the enzyme or a target lipid that is a product of the enzyme. A comparison of the quantified target lipid to a reference standard may indicate whether the lipid metabolizing enzyme is functioning properly. For example, PI3K is responsible for the phosphorylation of PtdIns(4,5)$P_2$ to PtdIns(3,4,5)$P_3$. PI3K is tightly regulated in normal tissues, but it is estimated to be constitutively active in up to 50% of human cancers. A cellular decrease of PtdIns(4,5)$P_2$, or a cellular increase of PtdIns(3,4,5)$P_3$, as compared to a reference standard, may be indicative of a lipid metabolism disorder and/or cancer. The reference standard may be the quantity present in a comparable sample from an individual with or without the disorder.

The lipid disorder may be any of Gaucher's disease, Tay-sachs disease, Niemann-Pick disease, Fabry's disease, a fatty acid oxidation disorder, such as MCAD deficiency. The cancer may be any of cowden's disease, breast cancer, thyroid cancer, endometrial cancer, pancreatic cancer, ovarian cancer, cervical cancer, colorectal cancer, glioblastoma, melanoma, prostate cancer, leukemia, lymphoma, gastric cancer, and/or lung cancer.

The present invention has multiple aspects, illustrated by the following non-limiting examples.

EXAMPLES

Example 1

Phosphatidylinositol-4,5-bisphosphate (PtdIns(4,5)$P_2$) Sensor

A specific sensor for PtdIns(4,5)$P_2$, which has been implicated in numerous cell processes, including membrane remodeling and regulation of membrane proteins and cytoskeletons, was made. Although PtdIns(4,5)$P_2$ is present mainly in the plasma membrane, its actual concentration, distribution, and spatiotemporal fluctuation has not been quantitatively determined. Traditionally, the PH domain of phospholipase Cd tagged with a fluorescent protein has been used as a cellular PtdIns(4,5)$P_2$ probe. However, PtdIns(4,5)$P_2$ imaging by the PH domain is known to be complicated by the ability of inositol-(1,4,5)-triphosphate, which is a hydrolysis product of PtdIns(4,5)$P_2$, to bind the domain and displace it from the membrane. Another PtdIns(4,5)$P_2$-selective protein was selected: the ENTH domain of epsin1 that is more stable and has lower affinity for inositol-(1,4,5)-triphosphate than the PH domain.

Figure 2:
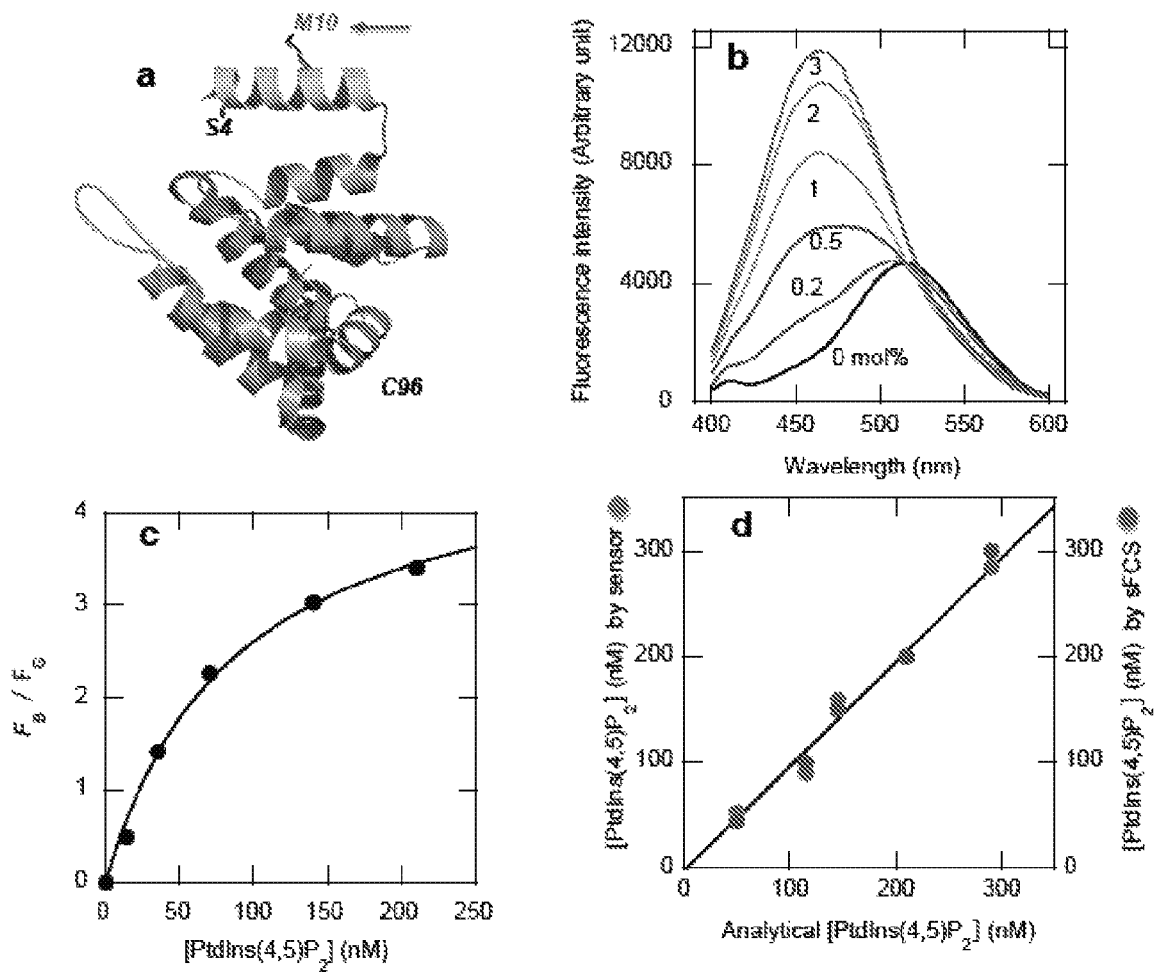
FIG. 2(a) shows the crystal structure of the epsin 1 ENTH is shown with mutated residues labeled. The arrow indicates the single site of chemical labeling.
FIG. 2(b) shows the fluorescence emission spectra of DAN-eENTH (500 nM) in the presence of POPC/POPS/PtdIns(4,5)$P_2$ (80-x:20:x) (x=0-3 mol %) large unilamellar vesicles (LUVs). The bottom line indicates the spectrum of the sensor without lipid, and the lines above are with vesicles with x=0, 0.25, 0.5, 0.75, 1, 1.5, 2, and 3 mol %, respectively.
FIG. 2(c) shows the plot of ($F_B/F_G$) versus [PtdIns(4,5)$P_2$] used as a calibration curve for ratiometric determination of [PtdIns(4,5)$P_2$]. The background correction for $F_B/F_G$ values was unnecessary because $F_B=0$ in the absence of PtdIns(4,5)$P_2$. Non-linear least-squares analysis of the plot using the equation; $(F_B/F_G)=(F_B/F_G)max/(1+Kd/[PtdIns(4,5)P_2])$ 12 yielded Kd=44±6 nM and $(F_B/F_G)$max=4.9±0.3. The theoretic curve was then constructed using these parameters.
FIG. 2(d) shows a comparison of [PtdIns(4,5)$P_2$] values determined by the ratiometric analysis of $F_B/F_G$ values and by sFCS with the analytical concentration of PtdIns(4,5)$P_2$. All [PtdIns(4,5)$P_2$] values are expressed in terms of the total lipid concentration in the bilayer.

The ENTH domain was engineered to introduce a single labeling site (M10C) on the membrane binding surface while removing an endogenous Cys (C96A). We also performed the S4W mutation to suppress its residual affinity for another lipid, phosphatidylinositol-3,4,5-trisphosphate (PtdIns(3,4,5)$P_3$) (PtdIns(4,5)$P_2$/PtdIns(3,4,5)$P_3$=4 for wild type and >10 for the mutant) and to enhance the overall affinity for PtdIns(4,5)$P_2$-containing membranes (ca. 4-fold) (Table 1). We then chemically labeled the engineered protein (eENTH: FIG. 2a) with the 2-dimethylamino-6-acyl-naphthalene (DAN) group, which exhibits a large increase in fluorescence emission at 450 nm when transferred from aqueous to non-polar environment. The resulting sensor, DAN-eENTH has about 3-fold higher affinity for PtdIns(4,5)$P_2$-containing vesicles than eENTH (i.e., 12-fold higher than the wild type; Table 1), indicating that the amphiphilic DAN fluorophore enhances the overall membrane affinity of the domain. Furthermore, unlike the wild type ENTH domain, DAN-eENTH showed no tendency to induce membrane deformation even at a high concentration (e.g., 10 μM). See FIG. 3.

With respect to FIG. 1, an L1 sensor chip was coated with POPC/POPS/PtdIns(4,5)P2 (77:20:3) LUVs. The proteins were incubated with a given concentration of IP3 for 5 minutes before injecting into the SPR instrument. Kinetic SPR measurements were performed in 20 mM Tris-HCL, pH 7.4, containing 0.16 KCl. Notice that 5 μM of IP3 inhibited the binding of the PLCδ PH domain to PtdIns(4,5)P2-containing vesicles by >70% while showing a minimal effect on that of DAN-eENT. A lower concentration of DAN-eENTH was used than that of PLCδ PH because the former has much higher affinity that the latter.

Figure 3:
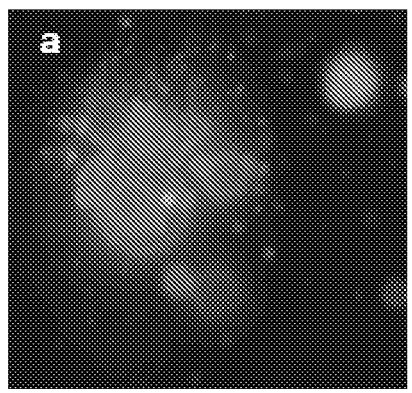
FIG. 3 shows vesicle deformation activity for epsin 1 ENTH domain (a) and DAN-eENTH(b).
Figure 3:
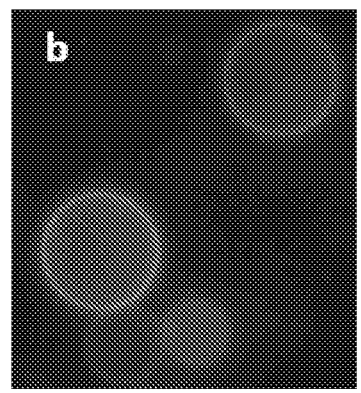

With respect to FIG. 3, POPC/POPE/POPS/PtdIns(4,5)P2/1,2-dipalmitoyl-sn-glycero-3-phospho-ethanolamine-N-lisamine rhodamine B sulfonyl (Rh-PE) (46.5:30:20:3:0.5) GUV were treated for 10 minutes with 10 μM of the proteins and the images of vesicles were monitored by Rh-PE fluorescence. All measurements were performed at 37° C. in 20 mM Tris-HCl buffer, pH 7.4, with 0.16 M KCl solution.

TABLE 1

| Membrane Affinities of the epsin1 ENTH domain and mutants | | | | |
|---|---|---|---|---|
| | Kd (nM) for PtdIns(4,5)$P_2$[a] | Kd (nM) for PtdIns(3,4,5)$P_3$[b] | Kd (NM) for PtdIns(3,4)$P_2$[c] | Kd (nM) for other phosphoinositide vesicles[d] |
| Wild Type | 50 +/− 8 | 210 +/− 40 | 180 +/− 30 | >1,000[e] |
| C96A | 53 +/− 7 | 200 +/− 45 | 190 +/− 42 | >1,000[e] |
| C96A/S4W (eENTH) | 12 +/− 3 | 150 +/− 20 | 140 +/− 23 | >1,000[e] |

TABLE 1-continued

Membrane Affinities of the epsin1 ENTH domain and mutants

|  | Kd (nM) for PtdIns(4,5)$P_2$[a] | Kd (nM) for PtdIns(3,4,5)$P_3$[b] | Kd (NM) for PtdIns(3,4)$P_2$[c] | Kd (nM) for other phosphoinositide vesicles[d] |
|---|---|---|---|---|
| DAN-eENTH | 4 +/− 1 | 44 +/− 8 | 50 +/− 10 | >1,000[e] |
| DAN-eENTH-L6A/R7A/R8A |  |  |  | >1,000[e] |
| PLCδ-PH | 180 +/− 20 | 480 +/− 60 | 350 +/− 50 | N.D.[f] |

With respect to Table 1,
[a]determined by the curve fitting of binding isotherms derived from equilibrium SPR sensorgrams for POPC/POPS/PtdIns(4,5)$P_2$ (77:20:3) LUVs in 20 mM Tris-HCL, pH 7.4, containing 0.16M KCl;
[b,c]determined in the same manner for POPC/POPS/PtdIns(3,4,5)$P_3$ (77:20:3) and POPC/POPS/PtdIns93,4)P2 (77:20:3) LUVs, respectively;
[d]determined for POPC/POPS/phosphoinositide (77:20:3) vesicles;
[e]no significant SPR response signal with the injection of 1 µM of a protein; and
[f]Not determined.

To check the feasibility of PtdIns(4,5)$P_2$ quantification using our sensor, the change in fluorescence emission of DAN-eENTH upon membrane binding was measured by spectrofluorometry. As shown in FIG. 2b, DAN-eENTH showed a dramatic blue-shift with a maximal increase in emission intensity (F) at 460 nm (F460) upon binding to large unilamellar vesicles (LUV) with varying composition of PtdIns(4,5)$P_2$; i.e., 1-palmitoyl-2-oleoyl-sn-3-phosphocholine (POPC)/1-palmitoyl-2-oleoyl-sn-3-phosphoserine (POPS)/PtdIns(4,5)$P_2$ (80-x:20:x), but not to similar vesicles containing any other phosphoinositide, e.g., POPC/POPS/PtdIns(3,4,5)P3 (80-x:20:x) (FIG. 4a), demonstrating high specificity. This favorable spectral change of DAN-eENTH suggests that [PtdIns(4,5)P2] can be determined either by intensity analysis at a single wavelength (e.g., F450; see FIG. 4b) or by ratiometric analysis at two wavelengths (e.g. F450/F520; see FIG. 4c).

Figure 4:
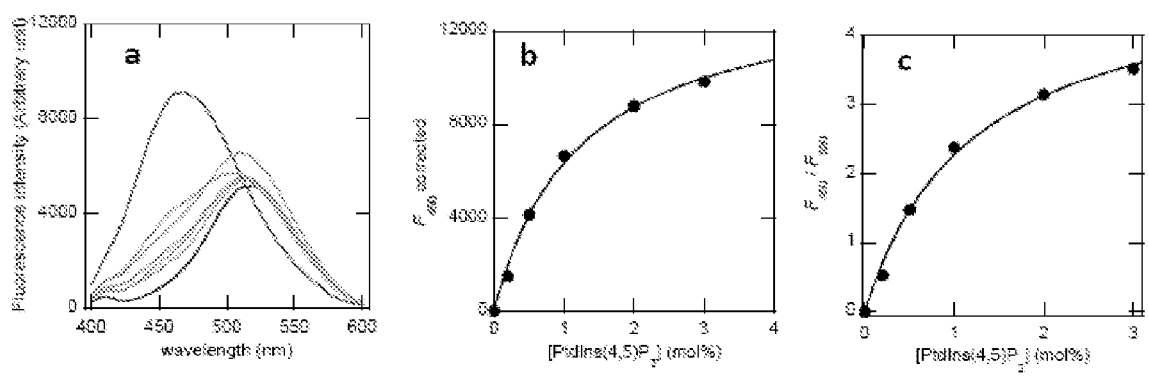
FIG. 4a shows a fluorescence emission spectra of DAN-eENTH (500 nM) in the presence of POPC/POPS/phosphoinositides (79:20:1) LUVs.
FIG. 4b shows the plot of background-corrected F450 versus[PtdIns(4,5)P2].
FIG. 4c shows a plot of F450/F520 versus [PtdIns(4,5)P2].

With respect to FIG. 4(a), the blue line indicates the spectrum without phosphoinositide, the red line with PtdIns(4,5)P2, and the orange lines with other phosphoinositides, including PtdIns(3,4,5)P3, PtdIns(3,5)P2, PtdIns(3,4)P2, PtdIns(3)P, PtdIns(4)P, and PtdIns(5)P. FIG. 4(b) shows non-linear least-squares analysis of the plot using the equation: F450+(F450)max/(1+Kd/[PtdIns(4,5)P2]) yielded Kd=1.2+/−0.2 mol % (=60+/−7 nM) and (F450)max=(1.4+/−0.1)×10³ (this calculation is based on the assumption that only half of total lipids are available to the sensor). The theoretic curve was then constructed using these parameters. For FIG. 3c, non-linear least-squares analysis of the plot using the equation; F450/F520=(F450/F520)max/1+Kd/[PtdIns(4,5)P2])
yielded Kd=1.2+/−0.2 mol % and (F450/F520)max=5.0+/−0.3.

Figure 5:
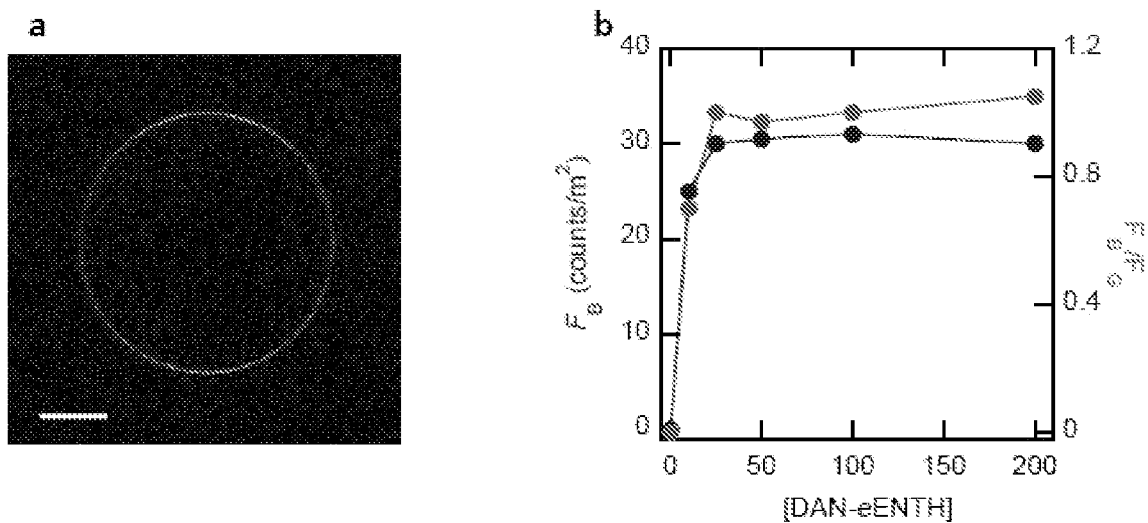
FIG. 5a shows an image of a GUV shown in the blue channel.
FIG. 5b shows FB and FB/FG as a function of [DAN-eENTH].

To calibrate the fluorescence microscope and the DAN-eENTH sensor for cellular PtdIns(4,5)$P_2$ quantification, we then determined by photon counting F values in the blue channel ($F_B$; observed with a 436±10 band pass filter) and the green channel (FG; observed with a 525±25 band pass filter) when DAN-eENTH was added to the solution of giant unilamellar vesicles (GUV) with the composition of POPC/POPS/PtdIns(4,5)$P_2$ (80-x:20:x with x=0-3). See FIG. 5a. Under our conditions, $F_B$ that originates exclusively from lipid-bound DAN-eENTH (i.e., the signal detectable only at the membrane) was negligible in the absence of PtdIns(4,5)P2, making background correction unnecessary. The resulting FB versus the surface concentration of PtdIns(4,5)$P_2$ ([PtdIns(4,5)P2]s; see Methods for calculation) (FIG. 2C) or (FB/FG) versus [PtdIns(4,5)$P_2$]s (FIG. 2d) calibration curve was used for ensuing PtdIns(4,5)$P_2$ quantification in GUV and in mammalian cells. With respect to FIG. 5, the bar indicates 10 µm and the radius of this GUV is measured as 20 mm. In FIG. 5(b), FB (blue) and FB/FG (red) values remain largely constant when [DAN-eENTH]>25 nM.

Figure 6:
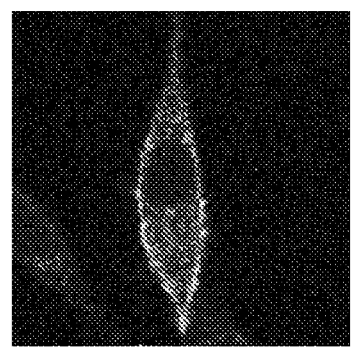
FIG. 6 shows cellular distribution of DAN-eENTH and its non-PtdIns(4,5)P2-binding mutant.
Figure 6:
Figure 7:
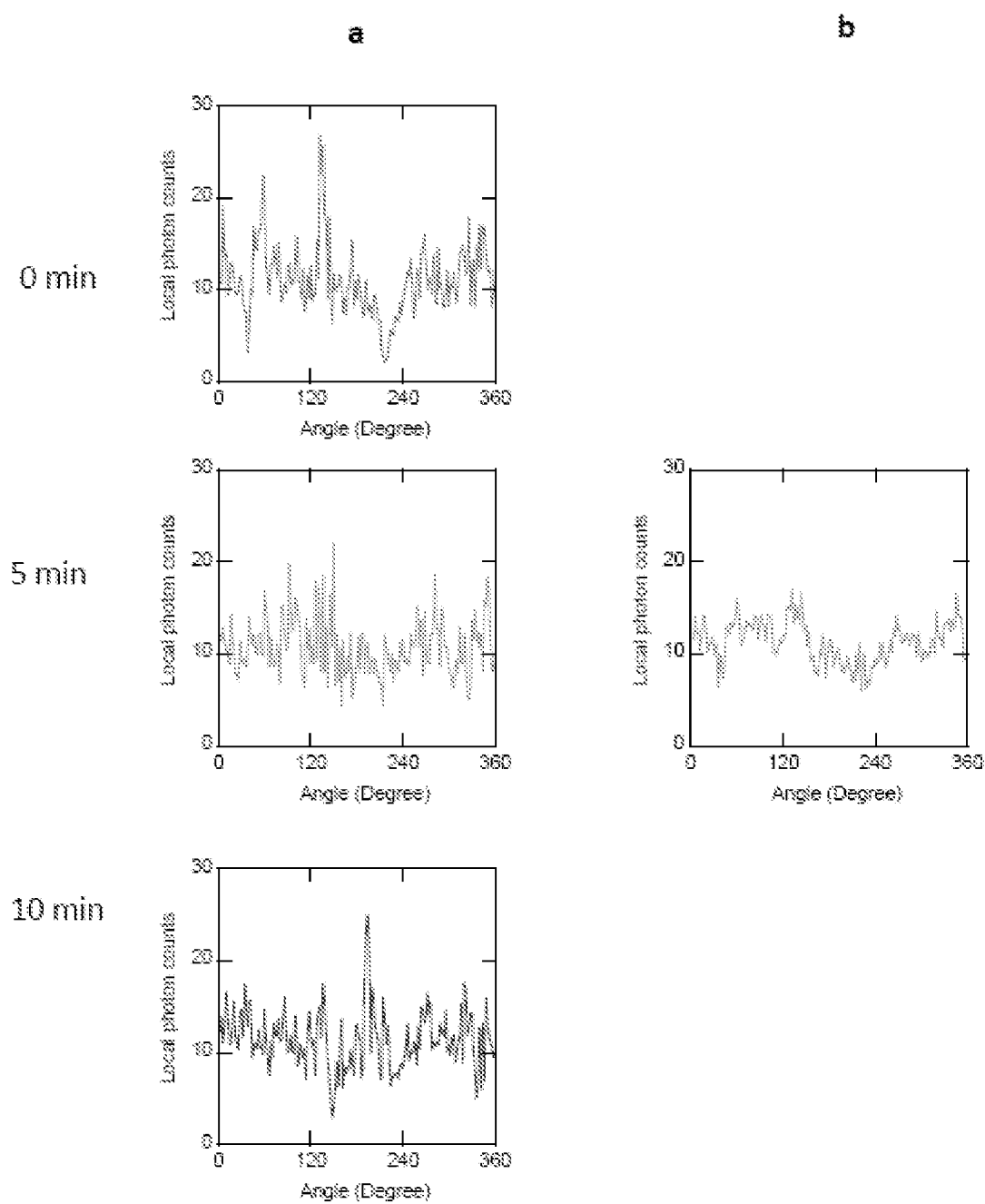
Figure 8:
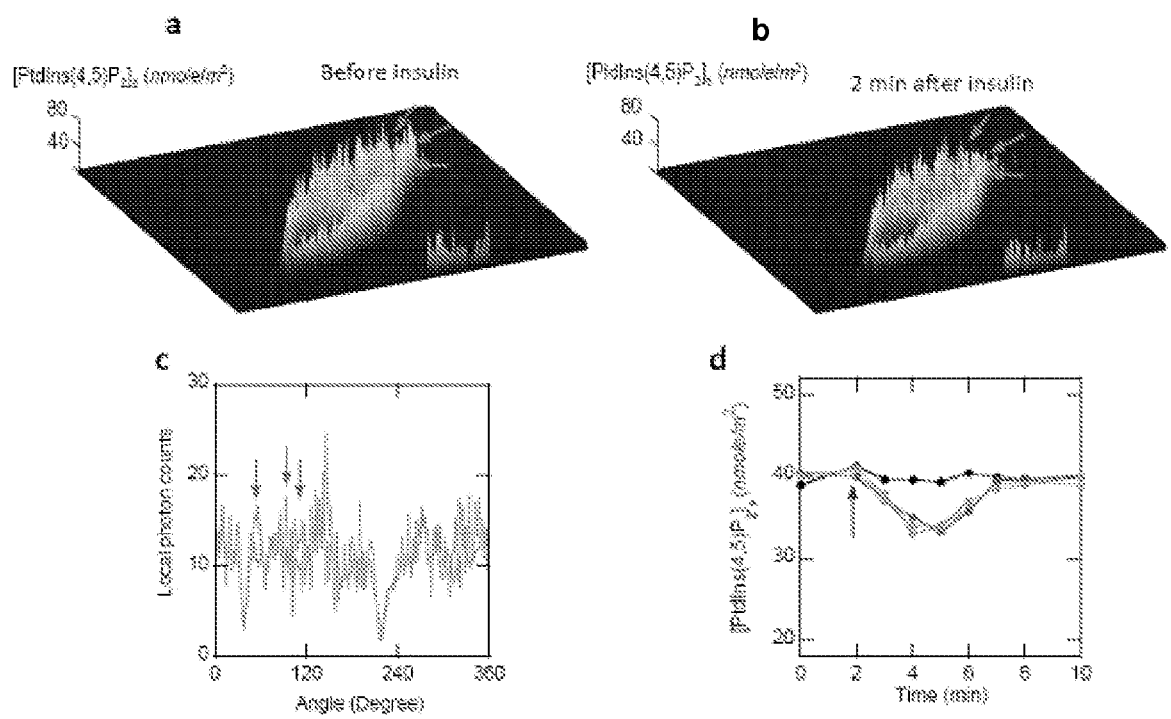
FIG. 8 shows the effects of insulin on PtdIns(4,5)P2 in NIH 3T3 cells. Spatially resolved quantification of [PtdIns(4,5)P2]s before (8a) and 2 minutes after (8b) 1 μM insulin stimulation by the single-channel analysis of FB using the calibration curve shown in FIG. 2c.
Figure 9:
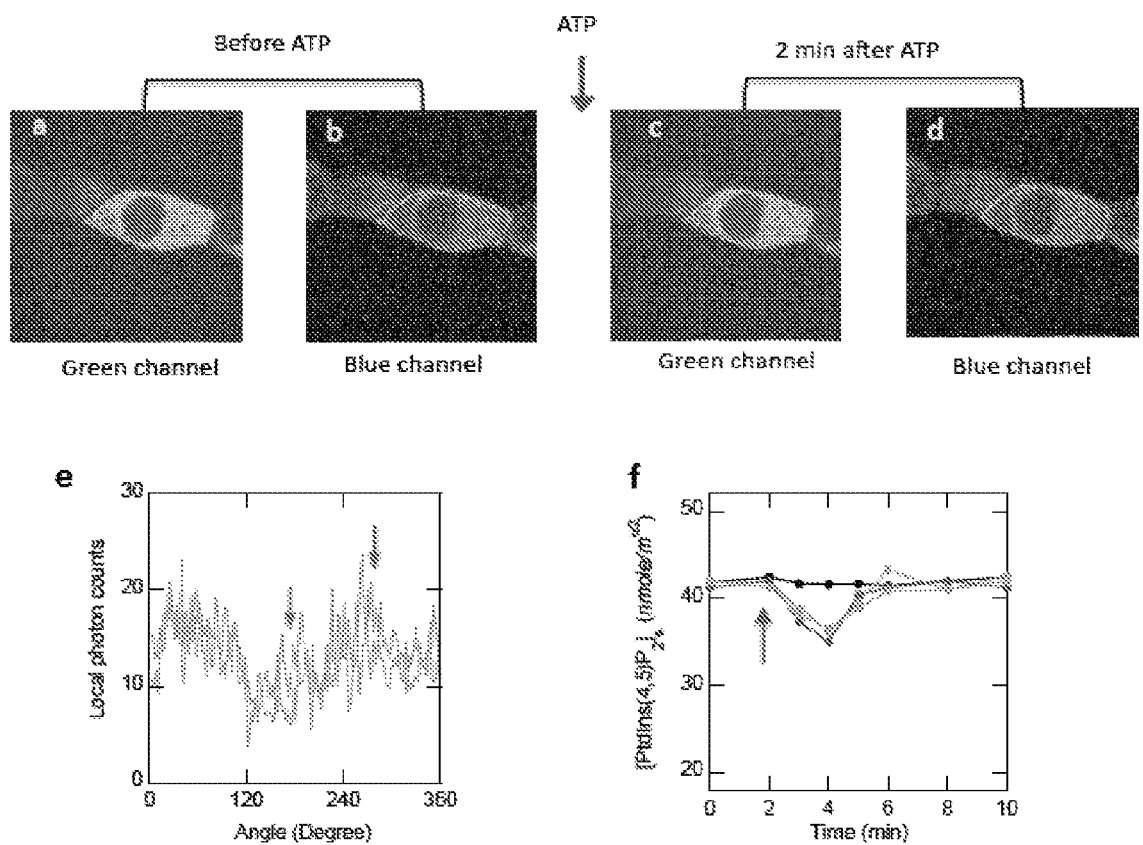
FIG. 9 shows the effects of ATP on PtdIns(4,5)P2 in NHI 3T3 cells.
Figure 10:
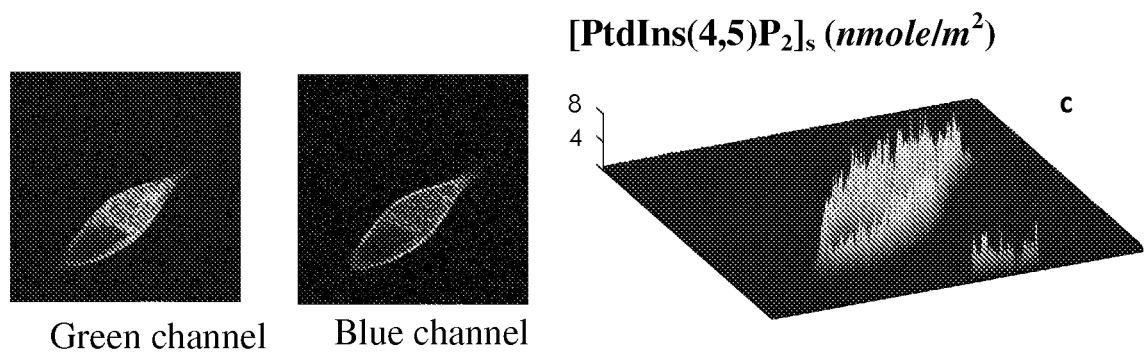
FIG. 10 shows in situ quantification of PtdIns(4,5)P2 in NIH 3T3 cell by DAN-eENTH sensor.

DAN-eENTH was delivered into NIH 3T3 cells by microinjection for live cell imaging and determined cellular [PtdIns(4,5)$P_2$] by the ratiometric analysis. The green channel (FIG. 10a) representing both PtdIns(4,5)$P_2$-bound and free DAN-eENTH illustrates that the sensor is successfully loaded into cells and randomly distributed in the cytosol, the nucleus, and the plasma membrane. However, the blue channel (FIG. 10b) representing PtdIns(4,5)$P_2$-bound DAN-eENTH shows that cellular PtdIns(4,5)$P_2$ is predominantly localized in the plasma membrane, consistent with previous reports. When a DAN-eENTH mutant devoid of PtdIns(4,5)$P_2$ affinity (See Table 1) was injected, it was mainly localized in the cytosol (See FIG. 6, wherein, under conditions in which DAN-eENTH is mainly enriched in the plasma membrane of NIH 3T3 cells, the mutant shows no detectable plasma membrane localization), showing that the PM localization of DAN-eENTH is driven by specific PtdIns(4,5)$P_2$ binding, not by binding to proteins on the PM. When [PtdIns(4,5)$P_2$]s in the PM was determined in a time-dependent manner by either single-channel 9FB) or ratiometric (FB/FG) analysis using the calibration curve (FIG. 2c or 2d), dramatic local heterogeneity of [PtdIns(4,5)$P_2$]s was clearly visible at a given time ((FIG. 9c). However, the local heterogeneity rapidly fluctuated over time (See FIG. 7a) and consequently, the time-averaged [PtdIns(4,5)$P_2$]s displayed relatively homogenous spatial distribution (FIG. 7b) with an average of 40 nmole/m² (which corresponds to 17 µM in bulk cellular concentration assuming that a NIH 3T3 cell is a sphere with 10 µm radius; see Methods). In FIG. 7, the different angles represent different locations in the plasma membrane. This demonstrates the sensitivity and power of our real-time in situ quantitative imaging and helps to solve the controversy regarding the local heterogeneity of PtdIns(4,5)$P_2$ in the PM. That is, PtdIns(4,5)P2 can be locally enriched, but only transiently, in the quiescent cells. The same trend was observed in >85% of 43 NIH 3T3 and 20 MDCk cells effectively microinjected with DAN-eENTH. Also, the change in [PtdIns(4,5)$P_2$]s was monitored in response to physiological stimuli, ATP and insulin. See FIGS. 8 and 9. With respect to FIG. 8b, 1 µM insulin stimulation by the single-channel analysis of FB using the calibration curve of 2C. Pseudo-coloring was used for images with red indicating the highest concentration and blue the lowest. With respect to 8d, three separate measurements are shown in different colors. Blue arrows indicate the timing of stimulation whereas red arrows indicate the locations of the largest local changes in [PtdIns(4,5)$P_2$]s. The insulin treatment caused modes ~10% reduction in spatially averaged [PtdIns(4,5)P$_2$]s in the plasma membrane; however, local effects were much more drastic in a few hot spots, underscoring the local nature of signaling. With respect to FIG. 9a, the green channel image of a representative cell shows relatively random cytosolic distribution of the DAN-eENTH sensor 10 minutes after microinjection. FIG. 9b shows a blue channel of the same cell showing plasma membrane localization of the sensor. The green (c) and blue (d) channel images of the same cell 2 minutes after 1 mM ATP treatment. FIG. 9e shows the angular profile representation of local [PtdIns(4,5)P$_2$]s before (orange) and 2 minutes after (cyan) ATP stimulation. FIG. 9f shows the time courses of spatially averaged [PtdIns(4,5)P$_2$]s in the plasma membrane upon 1 mM ATP treatment. Three separate measurements are shown in different colors. Blue arrows indicate the timing of stimulation whereas red arrows indicate the location of the largest local change in [PtdIns(4,5)P2]s. The effect of ATP is similar to that of insulin shown in FIG. 8.

[DAN-eENTH] was adjusted to give strong enough $F_B$ and $F_G$ signals for robust data analysis. The determination of [PtdIns(4,5)P$_2$] by the ratiometric analysis (see Methods for detailed description) of $F_B/F_G$ using the calibration curve (FIG. 2c) demonstrates strikingly heterogeneous distribution of PtdIns(4,5)P$_2$ in the plasma membrane with [PtdIns(4,5)P$_2$] ranging from 0 to 100 nM (FIG. 2c). When PtdIns(4,5)P$_2$ quantification was performed over time, major changes in spatial distribution of PtdIns(4,5)P$_2$ were clearly visible (FIG. 2d), suggesting the dynamic nature of PtdIns(4,5)P$_2$. Also, when [PtdIns(4,5)P$_2$] in the plasma membrane was lowered by ionomycin treatment, a majority of DAN-eENTH was released to the cytosol. The same trend was observed in >90% of 43 cells effectively microinjected with DAN-eENTH.

Collectively, these results show that the new molecular sensor allows robust quantification of PtdIns(4,5)P$_2$ in a spatiotemporally resolved manner. This strategy may be generally applicable to spatiotemporally resolved quantification of diverse cellular lipids using engineered lipid binding domains specific for individual lipids. With further development of new environment-sensitive fluorophores with desirable spectral properties, one can achieve more sensitive quantification of multiple lipids with minimal perturbation of physiological conditions.

Example 2

Phosphatidyl Serine Sensor

Figure 11:
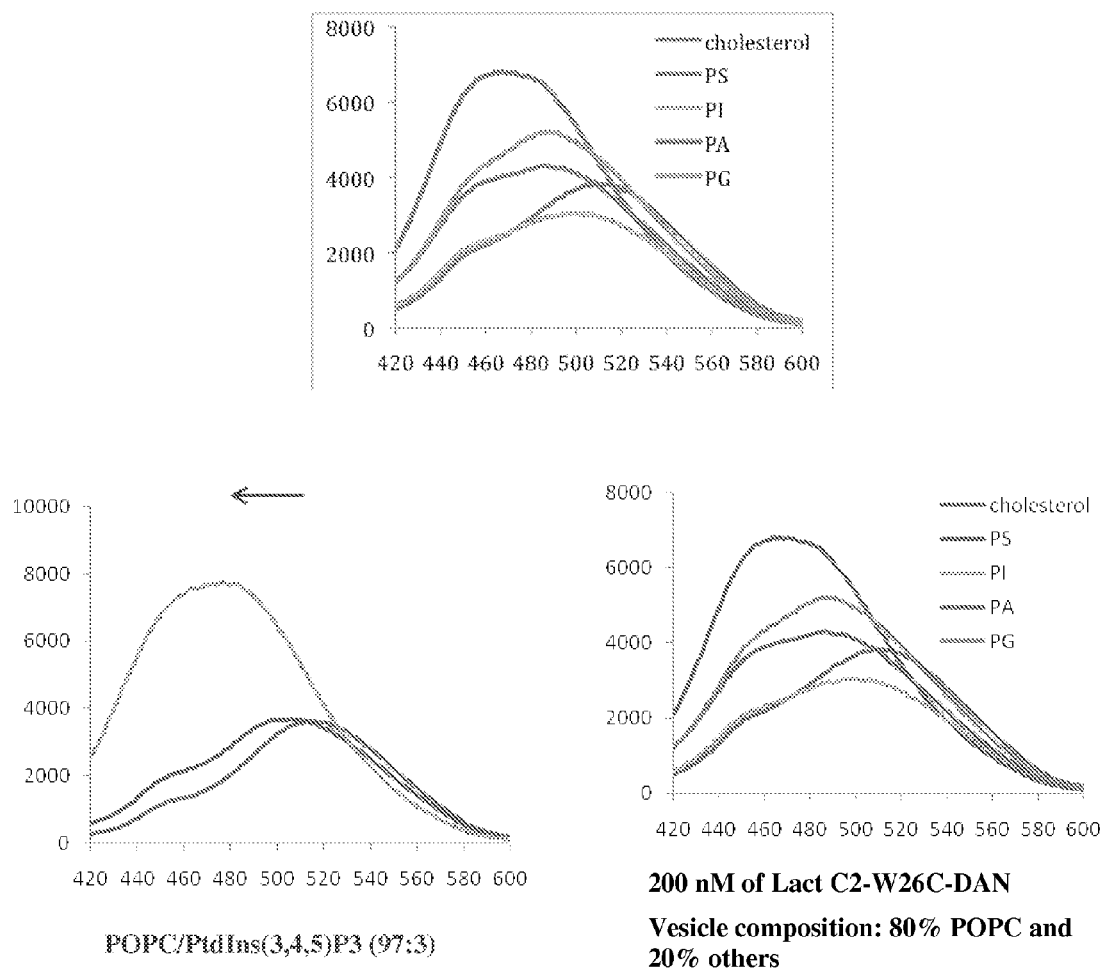
FIG. 11a shows the fluorescence emission spectra of DAN-Lact-C2 (W26C) (200 nM) in the presence of POPC/POPS (80:20) (green) and POPC/PtdIns(3,4,5)P3 (97:3) (red) LUVs. The blue line indicates the spectrum of the sensor without lipid.
FIG. 11b shows the fluorescence emission spectra of DAN-Lact-C2 (W26C) (200 nM) in the presence of POPC/POPS (80:20), POPC/POPA (80:20), POPC/POPG (80:20), POPC/POPI (80:20), and POPC/cholesterol (80:20) LUVs.

The Lact-C2 gene was amplified form the EGFP-C1-Lact-C2 vector (purchased from Haematologic Technologies, Inc.) and subsequently subcloned into the pET-21a vector (Novagen). All mutations were generated by PCR mutagenesis and verified by DNA sequencing. To generate a specific turn-on sensor for PS, the DAN group was chemically incorporated to a single free cystein residue introduced to different locations of Lact-C2. Among many engineered Lact-C2 constructs, W26C-DAN showed the best optical property (See FIG. 11(a)) and was thus selected as a specific PS sensor (see FIG. 11(b)). This constructed sensor allows for in situ quantification of PS concentration in the outer (when the sensor is added to the media) and the inner (when the sensor is microinjected) faces of the plasma membrane. We were able to quantify the PS concentration on the outer plasma membrane of apoptotic Jurkat T cells that is necessary for triggering phagocytosis by macrophages. PS concentration on the outer plasma membrane of platelets may also be quantified using this sensor.

Example 3

Phosphatidic Acid Sensor

Figure 12:
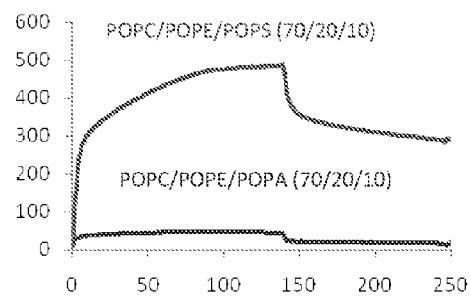
FIG. 12a-c shows the fluorescence emission spectra of DAN-Lact-C2 (W26C) and DAN-Lact-C2 (W26C, D80R, H83E/Q85K).
Figure 12:
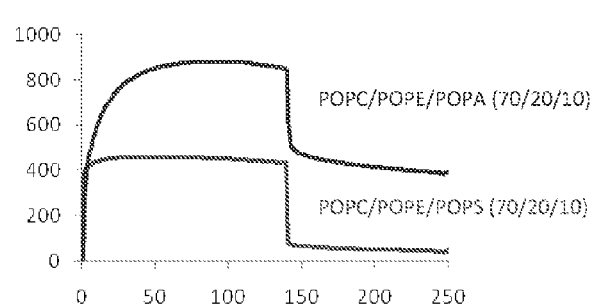
Figure 12:
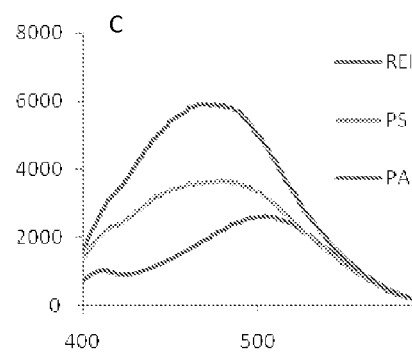

The Lact-C2 domain was converted into a PA-specific protein through protein engineering based on the crystal structure of Lact-C2 (J. Biol. Chem., (283)7230-7241 (2008)) and our molecular insight into PA and PS binding proteins. In the crystal structure, D80, H83, and Q85 interact with the serine head group of PS, so we mutated them to R, E, and K, respectively, to abrogate PS binding. Since PA has higher negative charge density without the head group, a mutant without PS binding may still interact with PA with high affinity. Our SPR analysis showed that the D80R/H83E/Q85K mutation converted the PS-specific Lact-C2 (FIG. 12(a)) into a PA-selective protein (FIG. 12(b)) and that DAN-Lact-C2-W26C/D80R/H83E/Q85K has desirable spectral properties. See FIG. 12(c). PA formation in NIH 3T3 cells in the presence of the phorbol ester, PMA, was successfully quantified.

Example 4

PtdIns(4,5)P$_2$ and Cellular Processes

Figure 13:
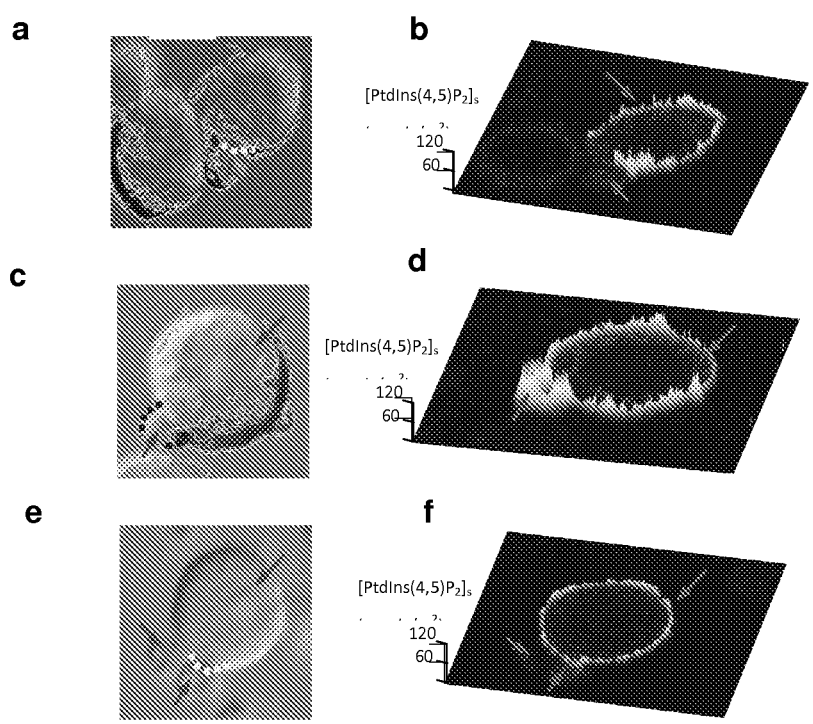
FIG. 13a shows a DIC image of a representative macrophage J774A.1 cell (green arrows) undergoing phagocytosis of an apoptotic Jurkat cell (red arrows).
FIG. 13b shows [PtdIns(4,5)$P_2$]$_s$ quantification for the macrophage. Notice that the PtdIns(4,5)P2 sensor was injected only into the marked macrophage cell. The Jurkat cell was subsequently phagocytosed by the macrophage.
FIG. 13c shows the DIC image of another macrophage at the later stage of phagcytosis.
FIG. 13d shows [PtdIns(4,5)$P_2$]$_s$ quantification for the macrophage. The expected location of the pseudopod is approximated from the [PtdIns(4,5)$P_2$]$_s$ data and is shown by blue dotted lines.
FIG. 13e shows the DIC images of macrophages that made contact with Jurkat cells but failed to phagocytose them.
FIG. 13f shows [PtdIns(4,5)$P_2$]$_s$ quantification for the macrophages. Cellular contact regions are marked with yellow dotted lines in DIC images.

Having established the local heterogeneity of PtdIns(4,5)P$_2$, the notion that the local PtdIns(4,5)P$_2$ concentration serves as a threshold for triggering cellular processes was tested. The quantitative correlation between local [PtdIns(4,5)P$_2$]$_s$ and the extent of phagocytosis that critically depends on PtdIns(4,5)P$_2$-mediated actin polymerization in phagocytic cells was assessed. The PtdIns(4,5)P$_2$ sensor was microinjected to >50 macrophage J774A.1 cells that made contact with apoptotic Jurkat T cells and determined [PtdIns(4,5)P$_2$]$_s$ in their PM while monitoring the progress of phagocytosis by differential interference contrast (DIC) imaging. See FIG. 13. We found that for ~40% of the macrophages, the local [PtdIns(4,5)P$_2$]$_s$ in the cell-cell contact region ranged from 60 to 80 nmole/m$^2$ (FIGS. 13a and 13b) and that these cells all successfully developed pseudopods surrounding Jurkat cells and completed the phagocytosis. Also, dramatic local enrichment of [PtdIns(4,5)P$_2$]$_s$ above 100 nmole/m2 was seen in the extended pseudopods. See FIGS. 13c and 13d. However, the rest of macrophages with [PtdIns(4,5)P$_2$]$_s$≤50 nmole/m2 throughout the contact region failed to develop PtdIns(4,5)P$_2$-enriched pseudopods. See FIGS. 13e to 13h. Together, these results clearly indicate the presence of the local threshold PtdIns(4,5)P$_2$ concentration (i.e., 60 nmole/m$^2$) in the initial cellular contact regions of phagocytic cells that is necessary for triggering actin polymerization and phagocytosis. This suggests that PtdIns(4,5)P$_2$ may also control other cellular processes differentially (and coincidently) by serving as variable thresholds.

Example 5

Materials and Methods

Thiol reactive acrylodan (6-acryloyl-2-dimethylaminonaphthalene) and thrombin were purchased from Invitrogen. 1-Palmitoyl-2-oleoyl-sn-glycero-3-phosphocholine (POPC) and 1-palmitoyl-2-oleoyl-sn-glycero-3-phosphoserine (POPS) were purchased from Avanti Polar Lipids. 1,2-di-palmitoyl derivatives of phosphatidylinositol-(4,5)-bisphosphate (PtdIns(4,5)P$_2$), phosphatidylinositol-(3,4,5)-trisphosphate (PtdIns(3,4,5)P3), and other phosphoinositides were from Cayman Chemical. A fluorescence labeled lipid, TMR-PtdIns(4,5)P$_2$ was from Invitrogen.

The Epsin1 ENTH domain (1-158 amino acids) was subcloned into the pGEX4T-1 vector and expressed as a C-terminal glutathione S-transferase (GST)-tagged protein. The ENTH domain amino acid sequence is as follows:

```
                                        (SEQ ID NO: 1)
MSTSSLRRQM KNIVHNYSEA EIKVREATSN DPWGPSSSLM

SEIADLTYNV VAFSEIMSMI WKRLNDHGKN WRHVYKAMTL

MEYLIKTGSE RVSQQCKENM YAVQTLKDFQ YVDRDGKDQG

VNVREKAKQL VALLRDEDRL REERAHALKT KEKLAQTA.
```

All mutations (S4W, M10C, and C96A) were performed by polymerase chain reaction mutagenesis and verified by DNA sequencing. eENTH may comprise the following sequence:

```
                                        (SEQ ID NO: 2)
MSTWSLRRQC KNIVHNYSEA EIKVREATSN DPWGPSSSLM

SEIADLTYNV VAFSEIMSMI WKRLNDHGKN WRHVYKAMTL

MEYLIKTGSE RVSQQAKENM YAVQTLKDFQ YVDRDGKDQG

VNVREKAKQL VALLRDEDRL REERAHALKT KEKLAQTA.
```

The Lact-C2 domain (1-158 amino acids) was subcloned into the modified pET21a vector and expressed as a C-terminal His$_6$-tagged protein. The Lact-C2 domain amino acid sequence is as follows:

```
                                        (SEQ ID NO: 3)
CTEPLGLKDN TIPNKQITAS SYYKTWGLSA FSWFPYYARL

DNQGKFNAWT AQTNSASEWL QIDLGSQKRV TGIITQGARD

FGHIQYVAAY RVAYGDDGVT WTEYKDPGAS ESKIFPGNMD

NNSHKKNIFE TPFQARFVRI QPVAWHNRIT LRVELLGC.
```

The mutations (W26C) was performed by polymerase chain reaction mutagenesis and verified by DNA sequencing. eLact-C2 may comprise the following sequence:

```
                                        (SEQ ID NO: 4)
CTEPLGLKDN TIPNKQITAS SYYKTCGLSA FSWFPYYARL

DNQGKFNAWT AQTNSASEWL QIDLGSQKRV TGIITQGARD

FGHIQYVAAY RVAYGDDGVT WTEYKDPGAS ESKIFPGNMD

NNSHKKNIFE TPFQARFVRI QPVAWHNRIT LRVELLGC.
```

All mutations (W26C, D80R, H83E, and Q85K) were performed by polymerase chain reaction mutagenesis and verified by DNA sequencing. eLact-C2 may comprise the following sequence:

```
                                        (SEQ ID NO: 5)
CTEPLGLKDN TIPNKQITAS SYYKTCGLSA FSWFPYYARL

DNQGKFNAWT AQTNSASEWL QIDLGSQKRV TGIITQGARR

FGEIKYVAAY RVAYGDDGVT WTEYKDPGAS ESKIFPGNMD

NNSHKKNIFE TPFQARFVRI QPVAWHNRIT LRVELLGC.
```

The PKCγ C1B domain (1-50 amino acids) was subcloned into the pET21a vector and expressed as a C-terminal His6-tagged protein. The C1B domain amino acid sequence is as follows:

```
                                        (SEQ ID NO: 6)
HKFRLHSYSS PTFCDHCGSL LYGLVHQGMK CSCCEMNVHR

RCVRSVPSLC.
```

All mutations (L24C and C33S) were performed by polymerase chain reaction mutagenesis and verified by DNA sequencing. ePKCγ-C1B may comprise the following sequence:

```
                                        (SEQ ID NO: 7)
HKFRLHSYSS PTFCDHCGSL LYGCVHQGMK CSSCEMNVHR

RCVRSVPSLC.
```

The cPLA2β C2 domain (1-120 amino acids) was subcloned into the modified pET21a vector and expressed as a N-terminal His6-tagged protein. The C2 domain amino acid sequence is as follows:

```
                                        (SEQ ID NO: 8)
TCLLTVRVLQAHRLPSKDLVTPSDCYVTLWLPTACSHRLQTRTVKNSSS

PVWNQSFHFRIHRQLKNVMELKVFDQDLVTGDDPVLSVLFDAGTLRAGE

FRRESFSLSPQGEGRLEVEFRL.
```

All mutations (L85C and V87K) were performed by polymerase chain reaction mutagenesis and verified by DNA sequencing. ecPLA2β-C2 may comprise the following sequence:

```
                                        (SEQ ID NO: 9)
TCLLTVRVLQ AHRLPSKDLV TPSDCYVTLW LPTACSHRLQ

TRTVKNSSSP VWNQSFHFRI HRQLKNVMEL KVFDQDCKTG

DDPVCSKLFD AGTLRAGEFR RESFSLSPQG EGRLEVEFRL.
```

The Btk-PH domain (1-169 amino acids) was subcloned into the modified pET21a vector and expressed as a N-terminal His6-tagged protein. The Btk-PH domain amino acid sequence is as follows:

```
                                        (SEQ ID NO: 10)
AAVILESIFL KRSQQKKKTS PLNFKKRLFL LTVHKLSYYE

YDFERGRRGS KKGSIDVEKI TCVETVVPEK NPPPERQIPR

RGEESSEMEQ ISIIERFPYP FQVVYDEGPL YVFSPTEELR

KRWIHQLKNV IRYNSDLVQK YHPCFWIDGQ YLCCSQTAKN

AMGCQILEN.
```

The mutations (E44C) was performed by polymerase chain reaction mutagenesis and verified by DNA sequencing. eStk-PH may comprise the following sequence:

```
                                        (SEQ ID NO: 11)
AAVILESIFL KRSQQKKKTS PLNFKKRLFL LTVHKLSYYE

YDFCRGRRGS KKGSIDVEKI TCVETVVPEK NPPPERQIPR
```

-continued

RGEESSEMEQ ISIIERFPYP FQVVYDEGPL YVFSPTEELR

KRWIHQLKNV IRYNSDLVQK YHPCFWIDGQ YLCCSQTAKN

AMGCQILEN.

E. coli BL21 RIL codon plus (Stratagene) cells were used for protein expression. Cells were grown in Luria broth media containing 100 μg/ml of ampicillin at 37° C. 0.1 mM of Isopropyl β-D-1-thiogalactopyranoside was added to induce over-expression of recombinant proteins when the OD600 reached 0.5-0.8 and cells were grown for additional 6 to 10 hours at 25° C. Cells were harvested by centrifugation and cell pellets were resuspended in 50 mM Tris-HCl buffer (pH 7.4) containing 160 mM KCl, 1 mM phenylmethanesulphonylfluoride, and 5 mM of dithiothreitol (DTT). Cells were lysed by sonication and the lysate was collected by centrifugation at 4° C. The GST-affinity resin (GenScript) for GST-tagged proteins or nickel-nitrilotriacetic acid resin (Qiagen, Valencia, Calif.) for $His_6$-tagged proteins was added into the cell lysate and the mixture was gently shaken for 30 minutes at 4° C. The mixture was applied to a column and the column was washed once with 50 mM Tris-HCl buffer (pH 7.4) containing 160 mM KCl and 5 mM of DTT to reduce thiol group, and washed several times with the same buffer without DTT to remove DTT. For DAN labeling, 100 μg of acrylodan was added to the column at this stage and incubated 16 hours at 4° C. The excess acrylodan was removed by washing the column with the buffer several times. Thrombin (Invitrogen) was added to column to remove the GST tag and the mixture was incubated at 4° C. for 10 hours. The labeled protein was eluted from the column by and the collected fractions were applied to ion exchange column. Purity and the concentration of the recombinant proteins were determined by sodium dodecylsulfate-polyacrylamide gel electrophoresis and bicinchoninic acid assay, respectively. The DAN labeling yield of eENTH, which was calculated as the molar ratio of DAN (determined spectrophotometrically at 391 nm using its extinction coefficient of 20,000 $cm^{-1}$ $M^{-1}$) to protein, was typically 60-70%.

LUVs were prepared by extrusion using a 100 nm-pore membrane. GUVs were prepared by electroformation. The lipid mixture were prepared in chloroform/methanol (3:1) at a total concentration of 0.4 mg/ml, then the lipid solution was spread onto the indium-tin oxide electrode surface and the lipid was dried under vacuum to form a uniform lipid film. Vesicles were grown in a sucrose solution (350 mM) while an electric field (3V, 20 Hz frequency) was applied for 5 hour at room temperature. After 1 to 2 ml of sucrose-loaded GUV solution was added into a well glued onto a coverslip that was placed on the microscope stage. The well contained 200 ml of 20 mM Tris-HCl buffer, pH 7.4, with 0.16 M KCl solution. The diameter of GUVs ranged from 5 to 30 μm.

Hitachi F-4500 spectrofluorometer was used for all cuvette-based fluorescence measurements. DAN-eENTH (typically 500 nM) was added to POPC/POPS/$PtdIns(4,5)P_2$ (80-x:20:x) (x=0-3 mol %) LUV and the emission spectra of DAN were measured with excitation wavelength set at 392 nm. The same measurements were repeated with LUVs made of different phosphoinositides, e.g., POPC/POPS/PtdIns(3,4,5)P3 (77:20:3).

In vitro calibration of our DAN-eENTH sensor was performed using GUVs composed of POPC/POPS/$PtdIns(4,5)P_2$ (80-x:20:x) (x=0-3 mol %). The bulk concentration of $PtdIns(4,5)P_2$ [$PtdIns(4,5)P_2$] was converted from the mol % in GUV using the total bulk lipid concentration of GUVs. Since only a half of total $PtdIns(4,5)P_2$ molecules (i.e., those in the outer monolayer) are accessible to the sensor, the effective [$PtdIns(4,5)P_2$] was taken as a half of total [$PtdIns(4,5)P_2$] for the calibration. These GUV were mixed with DAN-eENTH in the concentration range of 0-500 nM and spatiotemporally resolved fluorescence measurements were carried out at 37° C. using the custom-built multi-photon, multi-channel microscope that was described previously 13. All measurements were controlled and analyzed by the SimFCS. The DAN-eENTH was two-photon excited at 780 nm by a tunable Tsunami laser (Spectra Physics) and 436±10 (for blue channel) and the 525±25 (for green channel) band pass filters, respectively, were used to spectrally separate the fluorescence emission of the membrane-bound and the free DAN-eENTH species. At each time point, an image of 256×256 pixels was collected with the pixel dwell time of 32 millisecond using the Peltier-cooled 1477P style Hamamatsu photomultiplier tubes. An averaged image of a total of 10 frames was collected for each GUV of different $PtdIns(4,5)P_2$ concentration for further analysis by MATLAB. The photon counts data counts in blue ($F_B$) and green (FG) channels of the image were read into a 256×256 matrix to recreate the averaged image. Then a binary image mask was created using this image matrix by analyzing the photon count histogram of the image. The image matrix and its binary mask were multiplied to extract the photon counts only from GUV. The total photon counts were divided by the total number of pixels that forms only the GUV part of the image to get the average photon counts only from GUV. These average photon counts were used to prepare a calibration curve of the photon counts against the $PtdIns(4,5)P_2$ concentration.

The background correction for $F_B$ values was unnecessary because $F_B=0$ in the absence of $PtdIns(4,5)P_2$. Also, $F_G$ remained constant for both free and lipid-bound DAN-eENTH, which simplifies the ratiometric analysis (see below). The apparent Kd value of DAN-eENTH for $PtdIns(4,5)P_2$ in GUV was thus determined by ratiometric analysis. Kd and $(F_B/F_G)max$ values were calculated from non-linear least-squares analysis of the $F_B/F_G$ versus $[PtdIns(4,5)P_2]$ plot using the equation; $(F_B/F_G)=(F_B/F_G)max/(1+Kd/[PtdIns(4,5)P_2])$ and the theoretical calibration curve was constructed using these values (see FIG. 1c). Then, $[PtdIns(4,5)P_2]$ from unknown sample was calculated using the equation; $[PtdIns(4,5)P_2]=Kd(F_B/F_G)/\{(F_B/F_G)max-(F_B/F_G)\}$.

For POPC/POPS/TMR-$PtdIns(4,5)P_2$ (80-x:20:x) GUVs, $[PtdIns(4,5)P_2]$ was determined by the above ratiometric analysis using DAN-eENTH and independently by sFCS analysis of TMR-$PtdIns(4,5)P_2$. For each sFCS experiment, an orbit intersecting the surface of a GUV was selected with varying radius sizes (between 3 and 15 μm). In order to make sure that the GUV did not move during the measurement, images of the GUV were taken before and after the measurement. The data was collected with an excitation power of about 2 mW at the sample. The measurements were done with a sampling frequency of 64000 Hz and 1 millisecond per orbit. Before the sFCS measurements, the point spread function of the system was calibrated using 20 nM fluorescein in 10 mM Tris-HCl buffer, pH=9.0. In order to determine the waist of the point spread function, the diffusion rate of fluorescein was fixed to 300 μm2/sec and the waist was determined. All instrument control and data analysis were performed using the SimFCS software (Laboratory for Fluorescence Dynamics, University of California Irvine). Notice that the $[PtdIns(4,5)P_2]$ determined by sFCS represents the total concentration in the lipid bilayers.

NIH 3T3 cells were seeded into 8-well plates and grown at 37° C. in a humidified atmosphere of 95% air and 5% CO2 in Dulbecco's modified Eagle's medium (DMEM) (Invitrogen) supplemented with 10% (v/v) fatal bovine serum (Invitrogen). DAN-eENTH was delivered into the cells by microinjection using the Eppendorf InjectMan NI 2 system. All microscopy measurements and data analysis were performed as described above. For cell measurements, the minimal $F_B$ value was taken from the cytosol where PtdIns(4,5)P$_2$ is absent and $(F_B)$max was taken after the excess amount of exogenous PtdIns(4,5)P$_2$ was delivered to the cell by either microinjection or as vesicle formulation. Typically, $(F_B)$min was negligible and $(F_B)$max was comparable to that determined by the GUV calibration. Thus, the cellular [PtdIns(4,5)P$_2$] was determined from the observed $(F_B/F_G)$ values using the in vitro calibration curve determined using POPC/POPS/PtdIns(4,5)P$_2$ GUVs.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A fluorescent lipid-binding protein (FLBP), comprising a fluorophore and a lipid-binding protein comprising the amino acid sequence selected from the group consisting of SEQ ID NO: 2, SEQ ID NO: 4, SEQ ID NO: 5, SEQ ID NO: 7, SEQ ID NO: 9 and SEQ ID NO: 11.

2. The FLBP of claim 1, wherein the fluorophore is selected from the group consisting of 2-dimethylamino-6-acyl-naphthalene (DAN) and RED fluorophore.

3. The FLBP of claim 1, wherein the lipid-binding protein comprises the amino acid sequence of SEQ ID NO: 2.

4. The FLBP of claim 1, wherein the lipid-binding protein comprises the amino acid sequence of SEQ ID NO: 4.

5. The FLBP of claim 1, wherein the lipid-binding protein comprises the amino acid sequence of SEQ ID NO: 7.

6. The FLBP of claim 1, wherein the lipid-binding protein comprises the amino acid sequence of SEQ ID NO: 9.

7. The FLBP of claim 1, wherein the lipid-binding protein comprises the amino acid sequence of SEQ ID NO: 11.

8. The FLBP of claim 1, wherein DAN is chemically linked to amino acid C10 of SEQ ID NO: 2.

9. The FLBP of claim 1, wherein the lipid-binding protein comprises the amino acid sequence of SEQ ID NO: 5.

10. The FLBP of claim 9, wherein the lipid-binding protein is linked to DAN.

11. The FLBP of claim 4, wherein the lipid-binding protein is linked to DAN.

12. The FLBP of claim 5, wherein the lipid-binding protein is linked to DAN.

13. The FLBP of claim 6, wherein the lipid-binding protein is linked to DAN.

14. The FLBP of claim 7, wherein the lipid-binding protein is linked to DAN.

15. A method of quantifying a specific lipid in a cell membrane, comprising (a) introducing the FLBP of claim 1 to a cell; (b) imaging the cell; and (c) quantifying the lipid in the cell membrane.

16. The method of claim 15, wherein the specific lipid is phosphatidylinositol-4,5-bisphosphate (PtdIns(4,5)$P_2$).

17. The method of claim 16, wherein the FLBP is the FLBP of claim 6.

18. The method of claim 15, wherein the specific lipid is phosphatidic acid.

19. The method to claim 18, wherein the FLBP is the FLBP of claim 4.

20. The method of claim 15, wherein the specific lipid is phosphatidylserine.

21. The method of claim 15, wherein the specific lipid is diacylglycerol.

22. The method of claim 21, wherein the FLBP is the FLBP of claim 6.

23. The method of claim 15, wherein the specific lipid is cardiolipin.

24. The method of claim 23, wherein the FLBP is the FLBP of claim 7.

25. The method of claim 15, wherein the specific lipid is phosphatidylinositol-3,4,5-triphosphate (PtdIns(3,4,5)$P_3$).

26. The method of claim 25, wherein the FLBP is the FLBP of claim 8.

27. The method of claim 15, wherein the FLBP is administered by microinjection or transfection.

28. The method of claim 15, wherein step (b) is performed by an imaging system selected from the group consisting of fluorescence microscopy, confocal microscopy, and two-photon microscopy.

29. The method of claim 15, wherein the specific lipid is quantified by ratiometric analysis.

30. A method of diagnosing a lipid-metabolism-related disorder comprising (a) introducing the FLBP of claim 1 to a sample derived from a subject; (b) imaging the cells in the sample; (c) quantifying a target lipid in the cells; and (d) comparing the quantity identified in (c) with a reference standard, wherein the quantity of the target lipid present in the reference standard is the quantity present in a comparable sample from an individual with or without the disorder.

31. The method of claim 30, wherein the lipid-metabolism-related disorder is a PI-3 kinase-related disorder.

32. The method of claim 31, wherein the FLBP is the FLBP of claim 6.

33. The method of claim 32, wherein the target lipid is PtdIns(4,5)$P_2$.

* * * * *